US012733640B2

(12) United States Patent
Piotrowski et al.

(10) Patent No.: US 12,733,640 B2
(45) **Date of Patent: *Sep. 15, 2026**

(54) ANTIMICROBIAL FERULIC ACID DERIVATIVES AND USES THEREOF

(71) Applicant: Wisconsin Alumni Research Foundation, Madison, WI (US)

(72) Inventors: Jeff S. Piotrowski, Madison, WI (US); Fachuang Lu, Madison, WI (US); Mehdi Kabbage, Sun Prairie, WI (US); John Ralph, Madison, WI (US); Robert C. Landick, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,647

(22) Filed: Apr. 18, 2024

(65) Prior Publication Data

US 2024/0276985 A1 Aug. 22, 2024

Related U.S. Application Data

(63) Continuation of application No. 17/459,180, filed on Aug. 27, 2021, now Pat. No. 11,985,974, which is a continuation of application No. 14/703,337, filed on May 4, 2015, now abandoned.

(60) Provisional application No. 61/987,788, filed on May 2, 2014.

(51) Int. Cl.

| | |
|---|---|
| ***A01N 37/38*** | (2006.01) |
| ***A01N 43/08*** | (2006.01) |
| ***A01N 43/12*** | (2006.01) |
| ***A61K 31/192*** | (2006.01) |
| ***A61K 31/343*** | (2006.01) |
| ***A61K 45/06*** | (2006.01) |

(52) U.S. Cl.

CPC ............. *A01N 37/38* (2013.01); *A01N 43/08* (2013.01); *A01N 43/12* (2013.01); *A61K 31/192* (2013.01); *A61K 31/343* (2013.01); *A61K 45/06* (2013.01)

(58) Field of Classification Search

CPC ........ A01N 37/38; A01N 43/08; A01N 43/12; A61K 31/192; A61K 31/343; A61K 45/06

See application file for complete search history.

(56) References Cited

U.S. PATENT DOCUMENTS 11,985,974 B2 * 5/2024 Piotrowski ............ A01N 37/38

OTHER PUBLICATIONS

Bunzel et al. J. Sep. Sci. 2004, 27, pp. 1080-1086. (Year: 2004).*
Lattanzio et al. 1994, Italian Journal of Food Sci. No. 1, pp. 23-30. (Year: 1994).*
Abe M, Qadota H, Hirata A, Ohya Y (2003) Lack of GTP-bound Rholp in secretory vesicles of *Saccharomyces cerevisiae.* J Cell Biol 162(1):85-97.
Abe M, et al. (2001) Yeast 1,3-6-glucan synthase activity is inhibited by phytosphingosine localized to the endoplasmic reticulum. J Biol Chem 276(29):26923-26930.
Alexander BD, Perfect JR (1997) Antifungal resistance trends towards the year 2000. Implications for therapy and new approaches. *Drugs* 54(5):657-678.
Andrusiak K (2012) Adapting S. cerevisiae chemical genomics for identifying the modes of action of natural compounds. Masters thesis (University of Toronto, Toronto).
Altizer S, Ostfeld RS, Johnson PTJ, Kutz S, Harvell CD (2013) Climate change and infectious diseases: From evidence to a predictive framework. *Science* 341(6145): 514-519.
Avenot HF, Sellam A, Karaoglanidis G, Michailides TJ (2008) Characterization of mutations in the iron-sulphur subunit of succinate dehydrogenase correlating with Boscalid resistance in *Alternaria alternata* from California pistachio. *Phytopathology* 98(6):736-742.
Balashov, S. V., Park, S. & Perlin, D. S. Assessing Resistance to the Echinocandin Antifungal Drug Caspofungin in Candida albicans by Profiling Mutations in FKS1. Antimicrob. Agents Chemother. 50, 2058-2063 (2006).
Baranowski, J. D., Davidson, P. M., Nagel, C. W. & Branen, A. L. Inhibition of *Saccharomyces cerevisiae* by naturally occurring hydroxycinnamates. J. Food Sci. 45, 592-594 (1980).
Boyle E I, et al. (2004) GO:TermFinder-open source software for accessing Gene Ontology information and finding significantly enriched Gene Ontology terms associated with a list of genes. Bioinformatics 20(18): 3710-3715.
Bunzel, M., Ralph, J., Marita, J. M., Hatfield, R. D. & Steinhart, H. Diferulates as structural components in soluble and insoluble cereal dietary fibre. J. Sci. Food Agric. 81, 653-660 (2001).
Bunzel et al. Czech J. Food Sci., 2004, vol. 22, 64-67.
Bunzel et al. Semipreparative isolation of dehydrodiferulic and dehydrotriferulic acids as standard substances from maize bran. J. Sep. Sci. 27, (2004), 1080-1086.
Cassone A, Mason R E, Kerridge D (1981) Lysis of growing yeast-form cells of Candida albicans by echinocandin: A cytological study. Sabouraudia 19(2):97-110.
Chen L, et al. (2011) Trichoderma harzianum SQR-T037 rapidly degrades allelochemicals in rhizospheres of continuously cropped cucumbers. Appl Microbiol Biotechnol 89(5):1653-1663.
Cokol M, et al. (2011) Systematic exploration of synergistic drug pairs. Mol Syst Biol 7(2011):544.
Costanzo, M et al. The Genetic Landscape of a Cell. Science 327, 425-431 (2010).
DePristo, M. A et al. A framework for variation discovery and genotyping using next-generation DNA sequencing data. Nat. Genet. 43, 491-498 (2011).

(Continued)

*Primary Examiner* — Kara R. Mcmillian
(74) *Attorney, Agent, or Firm* — Daniel A. Blasiole; DeWitt LLP

(57) ABSTRACT

Antimicrobial diferulates, compositions containing same, and uses of same for inhibiting growth of microorganisms. The antimicrobial diferulates can be used alone or in combination with other antimicrobial agents to inhibit growth of microorganisms such as fungi, oomycetes, and other microorganisms having a glucan-containing cell wall. The antimicrobial diferulates can be included in pharmaceutical compositions for treatment of animals or included in agricultural compositions for treatment of plants, crops, and soils.

7 Claims, 10 Drawing Sheets

(56) References Cited

OTHER PUBLICATIONS

Fai PB, Grant A (2009) A rapid resazurin bioassay for assessing the toxicity of fungicides. Chemosphere 74(9):1165-1170.
FitzPatrick, M., Champagne, P., Cunningham, M. F. & Whitney, R. A. A biorefinery processing perspective: Treatment of lignocellulosic materials for the production of value-added products. Bioresour. Technol. 101, 8915-8922 (2010).
Free S J (2013) Fungal cell wall organization and biosynthesis. Adv Genet 81:33-82.
Fung S Y, Sofiyev V, Schneiderman J, Hirschfeld A F, Victor R E, Woods K, Piotrowski J S, Deshpande R, Li SC, de Voogd N J, Myers C L, Boone C, Andersen R J, Turvey S E. Unbiased screening of marine sponge extracts for anti-inflammatory agents combined with chemical genomics identifies girolline as an inhibitor of protein synthesis. ACS Chem Biol. Jan. 17, 2014; 9(1): 247-57.
Funk, C., Braune, A., Grabber, J. H., Steinhart, H. & Bunzel, M. Moderate Ferulate and Diferulate Levels Do Not Impede Maize Cell Wall Degradation by Human Intestinal Microbiota. J. Agric. Food Chem. 55, 2418-2423 (2007).
Garrett K A, Dendy S P, Frank E E, Rouse MN, Travers S E (2006) Climate change effects on plant disease: Genomes to ecosystems. Annu Rev Phytopathol 44(1):489-509.
Gnansounou, E. & Dauriat, A. Techno-economic analysis of lignocellulosic ethanol: A review. Bioresour. Technol. 101, 4980-4991 (2010).
Grabber et al., Model Studies of Ferulate-Coniferyl Alcohol Cross-Product Formatin in Primary Maize Walls: Implication for Lignification in Grasses, *J. Agric. Food Chem.* 2002, 50, 6008-6016.
Handbook of Pharmaceutical Salts, P.H. Stahl and C.G. Wermuch, Eds., © 2002, Verlag Helvitica Chemica Acta (Zurich, Switzerland). (Book).
Hatfield, R. D., Ralph, J. & Grabber, J. H. Cell wall cross-linking by ferulates and diferulates in grasses. J. Sci. Food Agric. 79, 403-407 (1999).
Heer D, Sauer U (2008) Identification of furfural as a key toxin in lignocellulosic hydrolysates and evolution of a tolerant yeast strain. Microb Biotechnol 1(6):497-506.
Ho, C. H. et al. Combining functional genomics and chemical biology to identify targets of bioactive compounds. Curr. Opin. Chem. Biol. 15, 66-78 (2011).
Imai K, Noda Y, Adachi H, Yoda K (2005) A novel endoplasmic reticulum membrane protein Rerl regulates chitin deposition in the cell wall of *Saccharomyces cerevisiae.* J Biol Chem 280(9):8275-8284.
Inoue S B, et al. (1995) Characterization and gene cloning of 1,3-6-D-glucan synthase from *Saccharomyces cerevisiae.* Eur J Biochem 231(3): 845-854.
Iwaki, A., Ohnuki, S., Suga, Y., Izawa, S. & Ohya, Y. Vanillin inhibits translation and induces messenger ribonucleoprotein (mRNP) granule formation in *Saccharomyces cerevisiae*: application and validation of highcontent, image-based profiling. PloS One 8, e61748 (2013).
Jayakody L N, Hayashi N, Kitagaki H (2011) Identification of glycolaldehyde as the key inhibitor of bioethanol fermentation by yeast and genome-wide analysis of its toxicity. Biotechnol Lett 33(2):285-292.
Jesch, S.A., Gaspar, M. L., Stefan, C. J., Aregullin, M.A. & Henry, S. A. Interruption of Inositol Sphingolipid Synthesis Triggers Stt4p-dependent Protein Kinase C Signaling. J. Biol. Chem. 285, 41947-41960 (2010).
Jo W J, et al. (2008) Identification of genes involved in the toxic response of *Saccharomyces cerevisiae* against iron and copper overload by parallel analysis of deletion mutants. Zoxicol Sci 101(1):140-151.
Johnson, M. E. & Edlind, T. D. Topological and Mutational Analysis of *Saccharomyces cerevisiae* Fks1. Eukaryot. Cell 11, 952-960 (2012).
Kiraz N, et al. (2010) Synergistic activities of three triazoles with caspofungin against Candida glabrata isoAug. 22, 2024 lates determined by time-kill, Etest, and disk diffusion methods. Antimicrob Agents Chemother 54(5):2244-2247.
Kitagaki H, Wu H, Shimoi H, Ito K (2002) Two homologous genes, DCW1 (YKLO046c) and DFGS, are essential for cell growth and encode glycosylphosphatidylinositol (GPI)-anchored membrane proteins required for cell wall biogenesis in *Saccharomyces cerevisiae.* Mol Microbiol 46(4): 1011-1022.
Kopecka M, Gabriel M (1992) The influence of congo red on the cell wall and (1-3)-beta-D-glucan microfibril biogenesis in *Saccharomyces cerevisiae.* Arch Microbiol 158(2):115-126.
Koppram, R., Tomas-Pejo, E., Xiros, C. & Olsson, L. Lignocellulosic ethanol production at high-gravity: challenges and perspectives. Trends Biotechnol. 32, 46-53 (2014).
Lau M W, Dale B E (2009) Cellulosic ethanol production from AFEX-treated corn stover using *Saccharomyces cerevisiae* 424A(LNH-ST). Proc Natl Acad Sci USA 106(5):1368-1373.
Leroch M, Kretschmer M, Hahn M (2011) Fungicide resistance phenotypes of Botrytis cinerea isolates from commercial vineyards in south west Germany. J Phytopathol 159(1):63-65.
Li, H. & Durbin, R. Fast and accurate short read alignment with Burrows-Wheeler transform. Bioinforma. Oxf. Engl. 25, 1754-1760 (2009).
Lu F, Wei L, Azarpira A, Ralph J. Rapid syntheses of dehydrodiferulates via biomimetic radical coupling reactions of ethyl ferulate. J Agric Food Chem. Aug. 29, 2012; 60(34):8272-7.
Mackie K A, Miiller T, Zikeli S, Kandeler E (2013) Long-term copper application in an organic vineyard modifies spatial distribution of soil micro-organisms. Soil Biol Biochem 65(2013):245-253.
Martin-Yken et al., *Saccharomyces cerevisiae* YCRO 17c/CWH43 encodes a putative sensor/transporter protein upstream of the BCK2 branch of the PKCI-dependent Cell wall integrity pathway, Yeast 2001, 18: 827-840.
Markovich, S., Yekutiel, A., Shalit, I., Shadkchan, Y. & Osherov, N. Genomic Approach to Identification of Mutations Affecting Caspofungin Susceptibility in *Saccharomyces cerevisiae.* Antimicrob. Agents Chemother. 48, 3871-3876 (2004).
Ohkuni, K., Okuda, A. & Kikuchi, A. Yeast Nap1-binding protein Nbp2p is required for mitotic growth at high temperatures and for cell wall integrity. Genetics 165, 517-529 (2003).
Ohnuki, S., Oka, S., Nogami, S. & Ohya, Y. High-Content, Image-Based Screening for Drug Targets in Yeast. PLOS ONE 5, e10177 (2010).
Ohnuki, S. et al. Analysis of the biological activity of a novel 24-membered macrolide JBIR-19 in *Saccharomyces cerevisiae* by the morphological imaging program CalMorph. FEMS Yeast Res. 12, 293-304 (2012).
Ohya, Y. et al. High-dimensional and large-scale phenotyping of yeast mutants. Proc. Natl. Acad. Sci. U.S.A 102, 19015-19020 (2005).
Okada, H., Ohnuki, S., Roncero, C., Konopka, J. B. & Ohya, Y. Distinct roles of cell wall biogenesis in yeast morphogenesis as revealed by multivariate analysis of high-dimensional morphometric data. Mol. Biol. Cell 25, 222-233 (2014).
Okada H, Ohya Y (2015) Cold Spring Harbor Protocols (Cold Spring Harbor Lab Press, Plainview, NY).
O'Maille P., Fungus against the Wall, *Nature,* 168, vol. 521 (May 14, 2015).
Palmqvist, E. & Hahn-Hagerdal, B. Fermentation of lignocellulosic hydrolysates. II: inhibitors and mechanisms of inhibition. Bioresour. Jechnol. 74, 25-33 (2000).
Parsons, A. et al. Exploring the Mode-of-Action of Bioactive Compounds by Chemical-Genetic Profiling in Yeast. Cell 126, 611-625 (2006).
Peltier, A. J. et al. Biology, Yield loss and Control of Sclerotinia Stem Rot of Soybean. J. Integr Pest Manag. 3, B1-B7 (2012).
Piotrowski, J.S. et al. Death by a thousand cuts: the challenges and diverse landscape of lignocellulosic hydrolysate inhibitors. Front. Microbiol. 5, (2014).
Piotrowski, J. S., Morford, S. L. & Rillig, M. C. Inhibition of colonization by a native arbuscular mycorrhizal fungal community via Populus trichocarpa litter, litter extract, and soluble phenolic compounds. Soi/ Biol. Biochem. 40, 709-717 (2008).

(56) References Cited

OTHER PUBLICATIONS

Piotrowski J S, Okada H, Lu F, Li S C, Hinchman L, Ranjan A, Smith D L, Higbee A J, Ulbrich A, Coon J J, Deshpande R, Bukhman Y V, Mcllwain S, Ong I M, Myers C L, Boone C, Landick R, Ralph J, Kabbage M, Ohya Y. Plant-derived antifungal agent poacic acid targets β-1,3-glucan. Proc Natl Acad Sci USA. Mar. 24 2015; 112(12):E1490-7.

Ralph J, Quideau S, Grabber J H, Hatfield R D (1994) Identification and synthesis of new ferulic acid dehydrodimers present in grass cell walls. J Chem Soc 23:3485-3498.

Ralph J, et al. (1998) Cell wall cross-linking in grasses by ferulates and diferulates.

Reinoso-Martin, C., Schiiller, C., SchuetzerMuehlbauer, M. & Kuchler, K. The yeast protein kinase C cell integrity pathway mediates tolerance to the antifungal drug caspofungin through activation of Slt2p mitogen activated protein kinase signaling. Eukaryot. Cell 2, 1200-1210 (2003).

Robinson D G, Chen W, Storey J D, Gresham D (2014) Design and analysis of Bar-seq experiments. G3 (Bethesda) 4(1):11-18.

Robinson M D, McCarthy D J, Smyth G K (2010) edgeR: A Bioconductor package for differential expression analysis of digital gene expression data. Bioinformatics 26(1): 139-140.

Rogers B, et al. (2001) The pleitropic drug ABC transporters from *Saccharomyces cerevisiae.* J Mol Microbiol Biotechnol 3(2):207-214.

S.M. Berge, et al., "Pharmaceutical Salts," J. Pharm. Sci., 66: p. 1-19 (Jan. 1977).

Santiago, R. et al. Diferulate Content of Maize Sheaths Is Associated with Resistance to the Mediterranean Corn Borer *Sesamia nonagrioides* (Lepidoptera: Noctuidae). J. Agric. Food Chem. 54, 9140-9144 (2006).

Sarma, B. K. & Singh, U. P. Ferulic acid may prevent infection of Cicer arietinum by Sclerotium rolfsii. WorldJ. Microbiol. Biotechnol. 19, 123-127 (2003).

Sato TK, et al. (2014) Harnessing genetic diversity in *Saccharomyces cerevisiae* for improved fermentation of xylose in hydrolysates of alkaline hydrogen peroxide pretreated biomass. Appl Environ Microbiol 80(2):540-554.

Skerker J M, et al. (2013) Dissecting a complex chemical stress: Chemogenomic profiling of plant hydrolysates. Mol Syst Biol 9:674.

Smith AM, et al. (2009) Quantitative phenotyping via deep barcode sequencing. Genome Res 19(10):1836-1842.

Sun, Y. & Cheng, J. Hydrolysis of lignocellulosic materials for ethanol production: a review. Bioresour. Technol. 83, 1-11 (2002).

Surma M A, et al. (2013) A lipid E-MAP identifies Ubx2 as a critical regulator of lipid saturation and lipid bilayer stress. Mol Cell 51(4):519-530.

Tawata et al. Synthesis and Antifungal Activity of Cinnamic Acid Esters. *Biosci. Biotech. Biochem.* vol. 60(5), (1996), 909-910.

Utsugi, T. et al. Movement of yeast 1,3-β-glucan synthase is essential for uniform cell wall synthesis. Genes Cells 7, 1-9 (2002).

Verna et al. A family of genes required for maintenance of cell wall integrity and for the stress response in *Saccharomyces cerevisiae.* Proc. Natl. Acad. Sci. USA, 1997, 94:13804-13809.

Vismeh, R. et al. Profiling of diferulates (plant cell wall cross-linkers) using ultrahigh-performance liquid chromatography-tandem mass spectrometry. Analyst 138, 6683-6692 (2013).

Watanabe D, Abe M, Ohya Y (2001) Yeast Lrg1lp acts as a specialized RhoGAP regulating 1,3-β-glucan synthesis. Yeast 18(10):943-951.

Westbrook J, Barter G E, Manley D K, West T H (2014) A parametric analysis of future ethanol use in the light-duty transportation sector: Can the US meet its Renewable Fuel Standard goals without an enforcement mechanism? Energy Policy 65(2014):419-431.

Wightwick A M, Salzman S A, Reichman S M, Allinson G, Menzies N W (2013) Effects of copper fungicide residues on the microbial function of vineyard soils. Environ Sci Pollut Res Int 20(3): 1574-1585.

Young, J. C., Hoogenraad, N. J., & Hartl, F. U. (2003). Molecular chaperones Hsp90 and Hsp70 deliver preproteins to the mitochondrial import receptor Tom70. Cell, 112(1), 41-50.

Yvert G, et al. (2013) Single-cell phenomics reveals intra-species variation of phenotypic noise in yeast. BMC Syst Biol 7(1):54.

* cited by examiner 8-5-DC 8-5-C 5-5

8-5-O 8-8-C 8-8-THF

4-O-5

8-O-4

8-8-O

Alexa594-ConA
Aniline blue
* p<0.05
% Cells with uniform staining
0
20
40
60
80
100
DMSO
Poacic acid (125 μg/mL)
DMSO
Poacic acid (125 μg/mL)
*

ANTIMICROBIAL FERULIC ACID DERIVATIVES AND USES THEREOF

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The present invention is directed to antimicrobial ferulic acid derivatives and their uses, particularly with regard to animal health and agriculture.

BACKGROUND

Fungal pathogens represent a threat to agriculture and animal health.

Fungal pathogens are one of the greatest economic threats to sustainable crop production. Fungal infections cause root rot, smut, powdery mildew, and a number of other diseases in garden plants, fruit trees, and general crops. Fungal infections destroy about 125 million tons of the top 5 food crops globally per year. One fungus, *Sclerotinia sclerotiorum*, is a significant agricultural pest of soybean, sunflower, and canola that is estimated to cause $250 million annually in damage in the US alone. In North America, the fungal pathogen landscape is changing as a warming climate brings novel pathogens from Central and South America.

The majority of fungicides used against economically significant pathogens are synthetic. The use of these synthetic antifungal agents has given rise to a concern that human pathogens may develop resistance to these compounds because of their prevalence in the environment. Given that fungal pathogens evolve fungicide resistance rapidly, new fungal pesticides are in increasing demand.

Because the majority of fungicides used against economically significant pathogens are synthetic, they are not compliant with USDA Organic Agriculture laws. Presently, $CuSO_4$ is used as an antifungal agent in organic agriculture, but there is a concern about the amount of copper leaching into the environment from its use. Few options exist for organic fungicides, and as such, an even greater demand exists for naturally derived fungicides for plant pathogens.

With regard to health, fungal infections are estimated to occur in over a billion people each year, and recent evidence suggests the rate is increasing. Fungi can infect almost any part of the body including skin, nails, respiratory tract, urogenital tract, and alimentary tract, or can be systemic. Anyone can acquire a fungal infection, but the elderly, critically ill, and individuals with weakened immunity, due to diseases such as HIV/AIDS or use of immunosuppressive medications, have a higher risk.

Increased use of antibiotics and immunosuppressive drugs such as corticosteroids are major factors contributing to higher frequency of fungal infections. Antibiotics and immunosuppressive drugs, by disrupting normal bacterial colonization and suppressing the immune system, create an environment within the body in which fungi can thrive.

Fungal infections can range in severity from superficial to life-threatening. For example, fungal infections affecting only the top layers of the skin are readily treatable and have a relatively limited impact on quality of life. However, if a fungal infection enters systemic circulation, consequences can be deadly.

A need exists for new antifungal agents to address the aforementioned problems in medicine and agriculture

SUMMARY OF THE INVENTION

The invention is directed antimicrobial diferulate compounds, antimicrobial compositions, and use of the compounds and compositions in inhibiting the growth of microorganisms. The compounds, compositions, and methods can be used pharmaceutically and agriculturally.

The antimicrobial diferulate compounds of the invention include compounds of Formula I and compounds of Formula II.

The compounds of Formula I are preferably selected from the group consisting of:

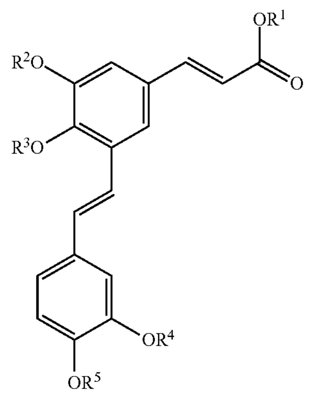

wherein $R^1$-$R^5$ are each independently selected from the group consisting of hydrogen, C1-C6 linear, branched, or cyclic alkyl, and C6 aryl; and a salt thereof. An exemplary version of a compound of Formula I is a compound selected from the group consisting of:

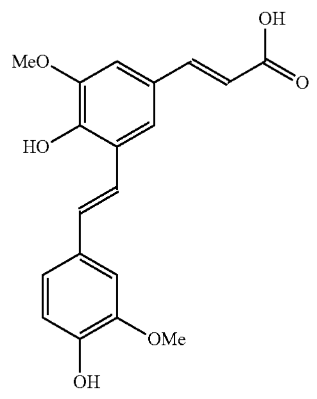 [SMILES: COc1cc(/C=C/c2cc(/C=C/C(=O)O)cc(OC)c2O)ccc1O]

and a salt thereof.

The compounds of Formula II are preferably selected from the group consisting of:

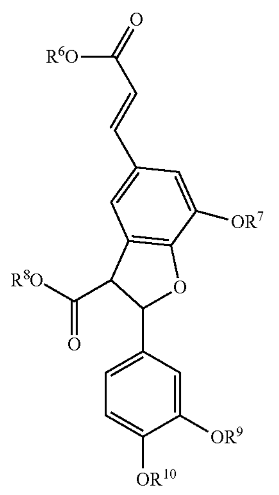

wherein $R^6$-$R^{10}$ are each independently selected from the group consisting of hydrogen, C1-C6 linear, branched, or cyclic alkyl, and C6 aryl; and a salt thereof. An exemplary version of a compound of Formula II is a compound selected from the group consisting of:

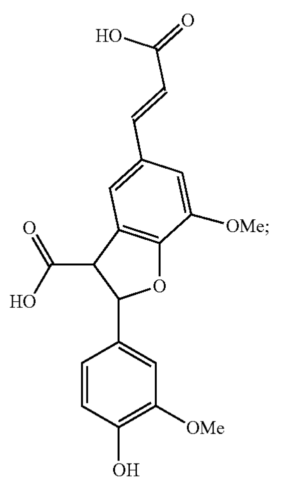 [SMILES: COc1cc(C2Oc3c(OC)cc(/C=C/C(=O)O)cc3C2C(=O)O)ccc1O]

and a salt thereof.

Some versions of the invention include an antimicrobial composition comprising an antimicrobial-effective amount of a substantially purified compound selected from the group consisting of a compound of Formula I, a compound of Formula II, and combinations thereof, in combination with an inert carrier. In some versions, the substantially purified compound comprises the compound of Formula I and the compound of Formula II. In some versions, the composition is substantially devoid of other diferulates commonly found in plant cell wall hydrolysates, such as any one or more diferulate compound selected from the group consisting of 5-5 diferulate, 8-5-O diferulate, 8-8-C diferulate, 8-8-THF diferulate, 4-O-5 diferulate, 8-O-4 diferulate, and 8-8-O diferulate. In some versions, the composition comprises from about 0.01% to about 95% by mass of the substantially purified compound.

In some versions, the composition comprises at least about 5% water by mass.

In various versions, the inert carrier may be a solid carrier, a semi-solid carrier, or a liquid carrier. If the inert carrier is a liquid carrier, the liquid carrier may comprise at least about 5% water by mass.

In some versions, the composition may comprise an antimicrobial compound in addition to the antimicrobial diferulates. The additional antimicrobial compound may comprise an antifungal compound. The additional antimicrobial compound may comprise a cell-wall targeting agent.

In various versions of the invention, the inert carrier in the composition comprises a pharmaceutically acceptable carrier and/or an agriculturally acceptable carrier.

Methods of the invention include inhibiting growth of a microorganism by contacting the microorganism with a substantially purified antimicrobial diferulate as described herein or a composition as described herein. Other methods of the invention include inhibiting microbial infection in a host by administering to the host an antimicrobial-effective amount of a substantially purified antimicrobial diferulate as described herein or a composition as described herein.

The microorganisms that may be inhibited include any microorganism comprising a glucan-containing cell wall. Exemplary microorganisms include fungi and oomycetes.

The antimicrobial diferulate or composition is preferably administered to a host suspected of being exposed to or infected with a microorganism comprising a glucan-containing cell wall, a fungus, and/or an oomycetes.

The antimicrobial diferulate or composition is preferably administered in a manner (e.g., in an amount and an administration route) such that the administering inhibits growth of a microorganism comprising a glucan-containing cell wall, a fungus, and/or an oomycetes.

In some versions, the host is an animal. In other versions, the host is a plant. In other versions, the host is a soil.

The objects and advantages of the invention will appear more fully from the following detailed description of the preferred embodiment of the invention made in conjunction with the accompanying drawings.

BRIEF DESCRIPTION OF THE DRAWINGS

FIG. 1A shows 8-5-DC diferulate. FIG. 1B shows 8-5-C diferulate. FIG. 1C shows 5-5 diferulate. FIG. 1D shows 8-5-O diferulate. FIG. 1E shows 8-8-C diferulate. FIG. 1F shows 8-8-THF diferulate. FIG. 1G shows 4-O-5 diferulate. FIG. 1H shows 8-O-4 diferulate. FIG. 1I shows 8-8-O diferulate.

DETAILED DESCRIPTION OF THE INVENTION

Figures 1A, 1B, 1C, 1D, 1E, 1F, 1G, 1H, 1I:
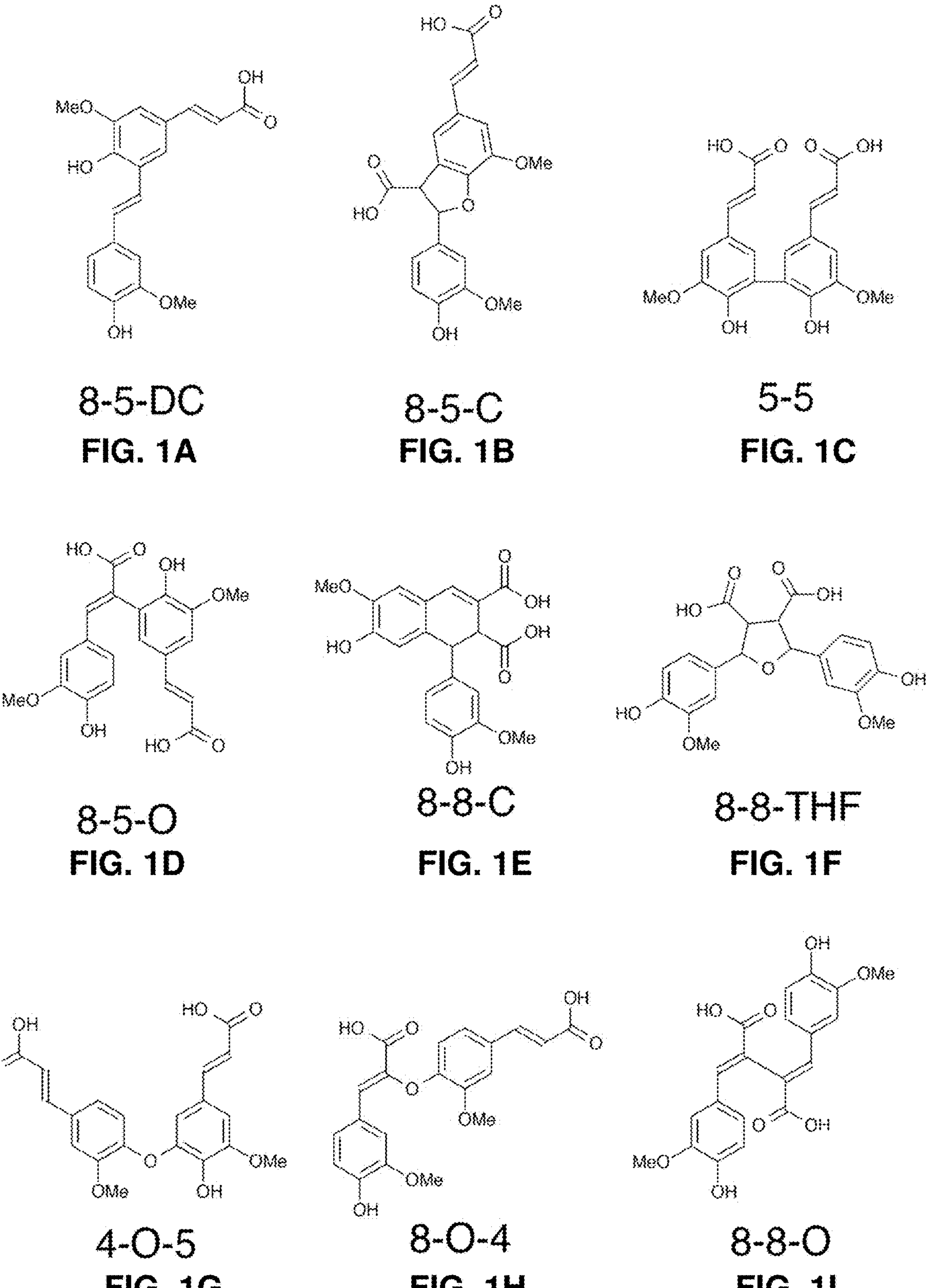
FIGS. 1A-1I. Diferulates found in lignocellulosic hydrolysates.

The compounds of the invention include antimicrobial diferulates characterized by Formula I and Formula II.

Compounds of Formula I have the structure:

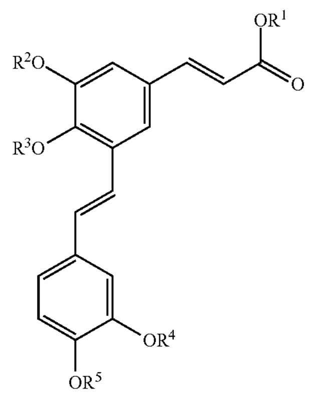

wherein $R^1$-$R^5$ are each independently selected from the group consisting of hydrogen, C1-C6 linear, branched, or cyclic alkyl, and C6 aryl, and include salts thereof. An exemplary version of a compound of Formula I is 8-5-decarboxylated (8-5-DC) diferulate, which has the following structure:

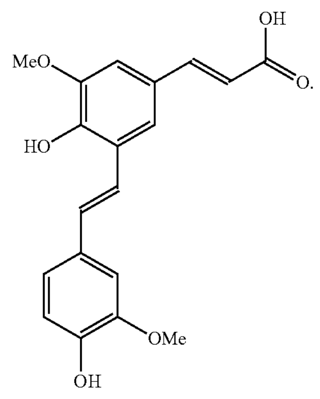 [SMILES: COc1cc(/C=C/c2cc(/C=C/C(=O)O)cc(OC)c2O)ccc1O]

Compounds of Formula II have the structure:

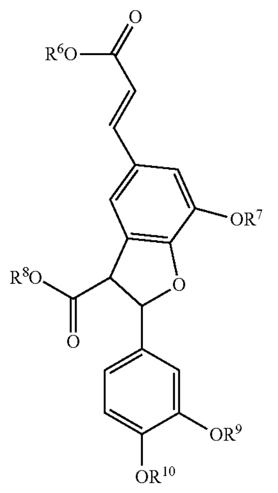

wherein $R^6$-$R^{10}$ are each independently selected from the group consisting of hydrogen, C1-C6 linear, branched, or cyclic alkyl, and C6 aryl, and include salts thereof. An exemplary version of a compound of Formula I is 8-5-cyclic (8-5-C) diferulate, which has the following structure:

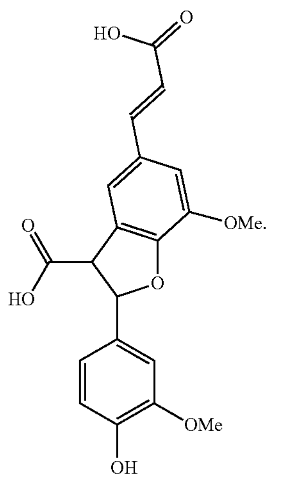 [SMILES: COc1cc(C2Oc3c(OC)cc(/C=C/C(=O)O)cc3C2C(=O)O)ccc1O]

The antimicrobial diferulates of the invention can be isolated from plant cell wall hydrolysates by methods known in the art. See Bunzel et al. *Czech J. Food Sci.,* 2004, vol. 22, 64-67. Alternatively, the antimicrobial diferulates of the invention can be synthesized by methods known in the art. See Ralph et al., *J Agric Food Chem.* 1998, 46:2531; Ralph et al., *J. Chem. Soc. Perkin Trans.,* 1994, 1:3485; and Lu et al. *J Agric Food Chem.* 2012, 60(34):8272-7.

Suitable salts are found in, for example, Handbook of Pharmaceutical Salts, P. H. Stahl and C. G. Wermuch, Eds., © 2002, Verlag Helvitica Chemica Acta (Zurich, Switzerland) and S. M. Berge, et al., "Pharmaceutical Salts," *J. Pharm. Sci.,* 66: p. 1-19 (January 1977), both of which are incorporated herein by reference. Other suitable salts include, without limitation, those derived from mineral acids and organic acids, explicitly including hydrohalides, e.g., hydrochlorides and hydrobromides, sulfates, phosphates, nitrates, sulfamates, acetates, citrates, lactates, tartrates, malonates, oxalates, salicylates, propionates, succinates, fumarates, malcates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, and the like. Base addition salts include those derived from alkali or alkaline earth metal bases or conventional organic bases, such as triethylamine, pyridine, piperidine, morpholine, N-methylmorpholine, and the like. In some versions of the invention, the salts are pharmaceutically suitable salts. The term "pharmaceutically suitable salt" refers to any salt whose counter-ions are non-toxic to the patient in pharmaceutical doses of the salts, so that the beneficial effects inherent in the free base or free acid are not vitiated by side effects ascribable to the counter-ions. In some versions of the invention, the salts are agriculturally suitable salts. The term "agriculturally suitable salt" refers to any salt whose counter-ions are non-toxic to the plant in effective doses of the salts, so that the beneficial effects inherent in the free base or free acid are not vitiated by side effects ascribable to the counter-ions.

The antimicrobial diferulates are preferably provided in substantially purified form. By "substantially purified form" is meant a non-naturally occurring, isolated form of the antimicrobial diferulates having a level of purity of at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or at least about 99% by mass from plant cell wall hydrolysate or product streams/batches of chemical synthesis processes. Purified and substantially purified forms of the antimicrobial diferulates can be obtained by purification of materials isolated by extraction from plant cell wall hydrolysates, or by purification of compounds obtained from a chemical synthesis process. Providing the antimicrobial diferulates in a substantially purified form does not preclude providing them in compositions comprising components that are not normally found with them in plant cell wall hydrolysates or product streams/batches of chemical synthesis processes, or even recombining the antimicrobial diferulates with other purified or semi-purified components that are normally found with them in plant cell wall hydrolysates or product streams/batches of chemical synthesis processes.

The antimicrobial diferulates in substantially purified form are preferably provided in a composition substantially devoid of non-antimicrobial diferulates. For example, the antimicrobial diferulates are preferably substantially purified from other diferulates found in plant cell wall hydrolysates or other diferulates that may be incidentally yielded in the synthesis process. The antimicrobial diferulates are preferably provided in a composition that is substantially devoid of, for example, one, some, or all of 5-5 diferulate, 8-5-O diferulate, 8-8-C diferulate, 8-8-THF diferulate, 4-O-5 diferulate, 8-O-4 diferulate, and 8-8-O diferulate. The structures of these diferulates are shown in FIGS. 1C-I. As used herein, "substantially devoid of" means having less than about 75%, 50%, 40%, 30%, 20%, 10%, 5%, 2.5%, or 1% by mass of one or more diferulates other than the antimicrobial diferulates described herein.

The antimicrobial diferulates may be provided and used in any combination, including compounds of Formula I (e.g., 8-5-DC diferulate and/or salts thereof) in the absence of compounds of Formula II (e.g., 8-5-C diferulate and/or salts thereof), compounds of Formula II (e.g., 8-5-C diferulate and/or salts thereof) in the absence of compounds of Formula I (e.g., 8-5-DC diferulate and/or salts thereof), or compounds of Formula I (e.g., 8-5-DC diferulate and/or salts thereof) in combination with compounds of Formula II (e.g., 8-5-C diferulate and/or salts thereof).

The antimicrobial diferulates may also or alternatively be provided and used in combination with one or more additional antimicrobial compounds. In preferred versions of the invention, the antimicrobial diferulates are combined with another antifungal compound. The antimicrobial diferulates may be combined with any effective antifungal compound. Chemicals used to control oomycetes are also referred to herein as antifungal compounds, as oomycetes use the same mechanisms as fungi for infection. Antifungal compounds are sometimes referred to in the art as "fungicides," "antifungals," or "antifungal medications."

Suitable antifungal compounds include cell-wall targeting agents. The antimicrobial diferulates have synergistic antifungal effects with cell-wall targeting agents. "Cell-wall targeting agent" refers to any agent that directly or indirectly disrupts the integrity of the cell wall, such as the fungal or oomycete cell wall.

Examples of cell-wall targeting agents include glucan synthesis inhibitors, such as β-glucan synthase inhibitors. Examples of β-glucan synthase inhibitors include the echinocandins, such as caspofungin, anidulafungin, and micafungin.

Other examples of cell-wall targeting agents are those that inhibit the yeast cell wall integrity signaling pathway. The yeast cell wall integrity signaling pathway is well-known in the art. Sec Verna et al. *Proc. Natl. Acad. Sci. USA,* 1997, 94:13804-13809. An exemplary schematic of the cell wall integrity signaling pathway is provided in FIG. 3, panel B. Any agent that inhibits, blocks, decreases expression of, or otherwise decreases the function of any of the factors in the pathway is suitable. Exemplary inhibitors of the yeast cell wall integrity signaling pathway include indolocarbazoles. An exemplary indolocarbazole is staurosporine.

Examples of other cell-wall targeting agents include ergosterol-targeting agents. Ergosterol-targeting agents inhibit the production of ergosterol or target ergosterol directly. Examples of ergosterol-targeting agents that inhibit the production of ergosterol include azoles, which target the ergosterol biosynthetic enzyme lanosterol 14alpha-demethylase. Examples of azoles include imidaozoles, such as bifonazole, butoconazole, clomidazole, clotrimazole, croconazole, econazole, fenticonazole, ketoconazole, isoconazole, miconazole, neticonazole, omoconazole, oxiconazole, sertaconazole, sulconazole, and tioconazole; triazoles, such as fluconazole, fosfluconazole, terconazole, hexaconazole, isavuconazole, itraconazole, posaconazole, voriconazole, and albaconazole; and thizoles, such as abafungin. Examples of ergosterol-targeting agents that target ergosterol directly include polyenes, which physically bind to ergosterol within the membrane, creating a polar pore in the membrane. Examples of polyenes include natamycin, nystatin, amphotericin B, and hamycin.

Examples of other cell-wall targeting agents include allylamines. Examples of allylamines include amorolfin, butenafine, naftifine, and terbinafine.

Yet other suitable antifungal compounds that may be combined with the antimicrobial diferulates include pyrimidine analogs/thymidylate synthase inhibitors such as flucytosine, mitotic inhibitors such as griseofulvin, and others, including bromochlorosalicylanilide, methylrosaniline, tribromometacresol, undecylenic acid, polynoxylin, chlorophetanol, chlorphenesin, ticlatone, sulbentine, ethylparaben, haloprogin, salicylic acid, selenium sulfide, ciclopirox, amorolfine, dimazole, tolnaftate, tolciclate, sodium thiosulfate, Whitfield's ointment, potassium iodide, taurolidine, tea tree oil, citronella oil, lemon grass, orange oil, patchouli, lemon myrtle, pentamidine, dapsone, and atovaquone.

Yet other suitable antifungal compounds that may be combined with the antimicrobial diferulates include acibenzolar-S-methyl, azoxystrobin, benalaxyl, benomyl, blasticidin-S, bromuconazole, captafol, captan, carbendazim, carboxin, carpropamid, chlorothalonil, the fungicidal compositions based on copper and copper derivatives such as copper hydroxide and copper oxychloride, cyazofamid, cyflufenamid, cymoxanil, cyproconazole, cyprodinyl, dichloran, diclocymet, diethofencarb, difenoconazole, diflumetorim, dimethomorph, dimoxystrobin, diniconazole, discostrobin, dodemorph, dodine, edifenphos, epoxyconazole, cthaboxam, ethirimol, fenarimol, fenbuconazole, fenhexamid, fenoxanil, fenpiclonil, fenpropidin, fenpropimorph, ferimzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenphos, iprodione, isoprothiolane, kasugamycin, kresoxim-methyl, mefenoxam, mepanipyrim, metalaxyl and its entantiomeric forms such as metalaxyl-M, metconazole, metiram-zinc, metominostrobin, metrafenone, nicobifen, oxadixyl, oxpoconazole, pefurazoate, penconazole, pencycuron, phosphorous acid and its derivatives such as fosetyl-A1, phthalide, picoxystrobin, probenazole, prochloraz, procymidone, propamocarb, propiconazole, pyraclostrobin, pyrimethanil, pyroquilon, quinoxyfen, silthiofam, simeconazole, spiroxamine, tebuconazole, tetraconazole, thiabendazole, thiflusamide, thiophanate, for example thiophanate-methyl, thiram, tiadinil, triadimefon, triadimenol, tricyclazole, tridemorph, trifloxystrobin, triticonazole, valinamide derivatives such as, for example, iprovalicarb, vinclozolin and zoxamide.

The antimicrobial diferulates are preferably included in a composition or administered in an antimicrobial-effective amount. As used herein, "antimicrobial-effective amount" and "effective amount" refer to amounts of the antimicrobial diferulate sufficient to inhibit growth of at least one type of microorganism. The term "inhibit" or grammatical variants thereof, used with regard to inhibiting growth of a type of microorganism, refers to any slowing of the growth of a population of the microorganism type. This may occur either through killing the microorganisms within the population or by slowing the reproduction rate of the microorganisms within the population. Unless explicitly specified, "inhibit" does not require complete prevention of reproduction or complete ablation of the population.

"Microbe" and "microorganism" are used herein interchangeably and refer to organisms conventionally falling under the scope of these terms. As used herein, however, "microbe" and "microorganism" also refer to all fungi, including yeasts, molds, unicellular fungi, and multicellular fungi, and oomycetes.

The antimicrobial diferulates of the invention are capable of inhibiting growth of microorganisms, more specifically, fungi, and even more specifically, fungi that are pathogenic to plants and animals. In particular, the antimicrobial diferulates of the invention are capable of inhibiting growth of microorganisms that contain a glucan-containing cell wall, such as a β-glucan-containing cell wall. β-Glucans are polysaccharides of D-glucose monomers linked by β-glycosidic bonds. β-Glucans are present in the cell walls of fungi, bacteria, oomycetes, and other microorganisms. As shown in the examples, the antimicrobial diferulates of the invention are thought to target the β-glucans in the cell wall as part of their antimicrobial activity.

The antimicrobial diferulates and compositions of the invention can be used to inhibit growth of a microorganism by contacting the microorganism with an antimicrobial diferulate and/or a composition containing an antimicrobial diferulate. Any method of placing the antimicrobial diferulate and/or the composition in contact with the microorganisms is acceptable.

The antimicrobial diferulates and compositions of the invention can be used to inhibit growth of a microorganism in a host by administering an antimicrobial diferulate and/or a composition containing an antimicrobial diferulate to the host. The antimicrobial diferulate and/or composition should be administered in a manner that results in the antimicrobial diferulate contacting any microorganism potentially present within or on the host. The administering can be used to treat infection of the microorganism already present in the organism or prevent infection from occurring. As used herein, "treat" refers to any level of amelioration of the infection or symptom associated with the infection. Accordingly, the antimicrobial diferulate and/or composition can be administered to a host known to harbor the microorganism, suspected of harboring the microorganism, or even suspected of being exposed to the microorganism.

"Host" refers to any object, whether living or non-living, that is capable of harboring a microorganism. Exemplary hosts include organisms, such as plants and animals. Exemplary plants include agricultural plants, as discussed in further detail below. Exemplary animals include mammals, such as humans. Other hosts may include non-living objects on or in which a fungus or other microorganism might be present and be capable of growing, such as a soil or field.

The antimicrobial diferulates alone or in combination with the one or more additional antimicrobial compounds are collectively referred to herein as "active agents." The active agents may be included with an inert carrier. The inert carrier may include any substance that does not substantially affect the antimicrobial effects of the active agents.

The active agents and the inert carrier may be specifically formulated as a pharmaceutical composition for pharmaceutical use or as an agricultural composition for agricultural use.

The compositions may comprise from about 0.001% to about 99% by mass of one or more of the antimicrobial diferulates. In various versions of the invention, the compositions may comprise at least about 0.001%, at least about 0.01%, at least about 0.1%, at least about 1%, at least about 5%, at least about 10%, at least about 20%, at least about 30%, at least about 40%, at least about 50%, at least about 60%, at least about 70%, at least about 80%, at least about 90%, at least about 95%, or at least about 99% by mass of one or more of the antimicrobial diferulates. Alternatively or additionally, the compositions may comprise up to about 0.01%, up to about 0.1%, up to about 1%, up to about 5%, up to about 10%, up to about 20%, up to about 30%, up to about 40%, up to about 50%, up to about 60%, up to about 70%, up to about 80%, up to about 90%, up to about 95%, or up to about 99% by mass of one or more of the antimicrobial diferulates.

In some versions of the invention, the inert carrier comprises water. The inert carrier may comprise water in an amount of at least about 1%, at least about 5%, at least about 10%, at least about 20%, at least about 30%, at least about 40%, at least about 50%, at least about 60%, at least about 70%, at least about 80%, at least about 90%, at least about 95%, or at least about 99% by mass. Accordingly, depending on the amount of active ingredients in the composition, the composition itself may comprise water in an amount of at least about 1%, at least about 5%, at least about 10%, at least about 20%, at least about 30%, at least about 40%, at least about 50%, at least about 60%, at least about 70%, at least about 80%, at least about 90%, at least about 95%, or at least about 99% by mass.

As described in further detail below, the inert carrier may comprise a solid carrier, a semi-solid carrier, or a liquid carrier. Such inert carriers may accordingly place the composition in a solid, semi-solid, or liquid form. Solid forms include capsules, cachets, tablets, boluses, lozenges, powders, etc. Semi-solid forms include gels, pastes, creams, ointments, etc. Liquid forms include syrups, solutions, liquid suspensions, etc.

The pharmaceutical compositions comprise one or more active agents together with a pharmaceutically acceptable carrier therefor. The carrier is pharmaceutically acceptable in the sense of being compatible with other ingredients in the particular composition and not deleterious to the recipient thereof. The compositions include those suitable for oral, topical, rectal, or parenteral (including subcutaneous, intramuscular, intradermal and intravenous) administration.

The pharmaceutical compositions may comprise the active agents in unit dosage form. The term "unit dosage" or "unit dose" is denoted to mean a predetermined amount of the active agents sufficient to be effective for treating each of the indicated activities. Preferred unit dosage formulations are those containing a daily dose, daily sub-dose, or an appropriate fraction thereof, of the active agents.

The pharmaceutical compositions may be prepared by any of the methods well known in the art of pharmacy. Methods include the step of bringing the active agents into association with the carrier. In general, the compositions are prepared by uniformly and intimately bringing the active agents into association with a liquid or solid carrier and then, if necessary, shaping the product into the desired unit dosage form.

Compositions of the present invention suitable for oral administration may be presented in a discrete solid form, e.g., as capsules, cachets, tablets, boluses, lozenges and the like, each containing a predetermined amount of the active agent; in powder or granular form; or in liquid form, e.g., as a collyrium, suspension, solution, syrup, elixir, emulsion, dispersion and the like. A tablet may be made by compression or molding, optionally with one or more accessory ingredients. Compressed tablets may be prepared by compressing in a suitable machine the active agents in a free-flowing form, e.g., a powder or granules, optionally mixed with accessory ingredients or excipients, e.g., binders, lubricants, inert diluents, surface active or dispersing agents. Molded tablets may be made by molding in a suitable machine, a mixture of the powdered active agents with any suitable carrier.

Compositions suitable for parenteral administration may comprise a sterile injectable or infusable preparation of the active agents in, for example, a solution which is preferably isotonic with the blood of the recipient. Useful formulations also comprise concentrated solutions or solids containing the active agents which upon dilution with an appropriate diluent give a solution suitable for parenteral administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Compositions suitable for topical or local application (including ophthamological administration) comprise the active agents formulated into pharmaceutically-acceptable topical carriers by conventional methodologies. Common formulations include drops, collyriums, aerosol sprays, lotions, gels, ointments, plasters, shampoos, transferosomes, liposomes and the like. In topical formulations, the active agents are preferably utilized at concentrations of from about 0.1% to about 5.0% by weight.

Compositions suitable for rectal administration may comprise a suppository, preferably bullet-shaped, containing the active agents and a pharmaceutically-acceptable carrier therefor such as hard fat, hydrogenated cocoglyceride, polyethylene glycol and the like. Compositions suitable for rectal administration may alternatively comprise the active agent and pharmaceutically-acceptable liquid carriers therefor such as 50% aqueous ethanol or an aqueous salt solution which is physiologically compatible with the rectum or colon. In rectal formulations, the active agents are preferably utilized at concentrations of from about 0.1 to about 10% by weight.

Compositions suitable for inhalation may include a micronized powder or liquid formulation having a particle size in the range of from about 5 microns or less to about 500 microns, for rapid inhalation through the nasal or oral passage from a conventional inhalation squeeze or spray container. Suitable liquid nasal compositions include conventional nasal sprays, nasal drops and the like comprising solutions of the active agents and optional adjuvants.

In addition to the aforementioned ingredients, the pharmaceutical compositions of this invention may further include one or more optional accessory ingredients(s) utilized in the art of pharmaceutical formulations, e.g., diluents, buffers, flavoring agents, colorants, binders, surfactants, thickeners, lubricants, suspending agents, preservatives (including antioxidants) and the like.

The amount of active agent required to be effective for each of the indicated activities will vary with the individual animal being treated and is ultimately at the discretion of the medical or veterinary practitioner. The factors to be considered include the species and sex of the animal, the condition being treated, the route of administration, the nature of the formulation, the animal's body weight, surface area, age and general condition, and the particular agents to be administered.

In general, the pharmaceutical compositions of this invention contain from about 0.005 to about 500 mg and, preferably, from about 0.05 to about 350 mg of each active agent, preferably in a unit dosage form, for each of the indicated activities. A suitable effective dose may be in the range of about 0.001 to about 200 mg/kg body weight per day for each active agent, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

The antimicrobial diferulates and the pharmaceutical compositions comprising the antimicrobial diferulates can be used to inhibit growth of a number of microorganisms and thereby treat or prevent their associated diseases. Examples of microorganisms that can be treated with the antimicrobial diferulates and the pharmaceutical compositions described herein include bacteria, fungi, or any other microorganism comprising a glucan-containing cell wall. Examples include fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause *pneumocystis* pneumonia; and fungi of the genus *Sporothrix*, such as *Sporothrix schenckii*, which cause sporotrichosis.

The agricultural compositions comprise one or more active agents together with a agriculturally acceptable carrier therefor. A carrier is agriculturally acceptable in the sense of being compatible with other ingredients in the particular composition and not deleterious to the intended host.

The agricultural compositions of the invention may be in the form of an aerosol, bait (ready-to-use), concentrate for preparation of baits, stock bait, suspension of capsules, cold fogging concentrate, dustable powder, emulsifiable concentrate, aqueous/aqueous type emulsion, oil/inverse type emulsion, encapsulated granule, fine granule, suspension concentrate for seed treatment, compressed gas, gas generating product, grain bait, granular bait, granule, hot fogging concentrate, macrogranule, microgranule, oil-dispersible powder, oil miscible suspension concentrate, oil-miscible liquid, paste, plant rodlet, plate bait, powder for dry seed treatment, scrap bait, coated seed, smoke candle, smoke cartridge, smoke generator, smoke pellet, smoke rodlet, smoke tablet, smoke tin, soluble concentrate, soluble powder, solution, solution for seed treatment, suspension concentrate (flowable concentrate), tracking powder, ultra-low volume liquid, ultra-low volume suspension, vapor-releasing product, water-dispersible granules or tablets, water dispersible powder for slurry treatment, water-soluble granules or tablets, water-soluble powder for seed treatment, or wettable powder.

These agricultural compositions cover not only compositions which are ready to be applied to a plant to be treated by means of a suitable device, such as a spraying device, but also commercial concentrated compositions which have to be diluted before applying to the plant.

The agricultural compositions may be administered to the plant by applying directly to growing plants, to sites where plants are grown, or to the plant seeds by coating or film-coating of seeds. The agricultural compositions may be administered in liquid, aerosol, solid (i.e., powder, etc.), semi-solid (e.g., gel, etc.), or other form. The agricultural compositions may be applied directly to the vegetation and in particular to the leaves infested or capable of being infested with the microorganism. The compositions may also be added to the irrigation water. This irrigation may be an irrigation using sprinklers. Other methods of administering agricultural compositions are known in the art.

In the agricultural compositions, the inert carrier is preferably a solid or liquid filler or diluent, adjuvant, surfactant, or equivalent, which is suitable for the desired use and which is acceptable for uses in agriculture. The inert carrier may comprise protective colloids, adhesives, thickeners, thixotropic agents, penetrating agents, oils for spraying, stabilizers, sequestering agents and the like. More generally, the antimicrobial diferulates of the invention can be combined with any solid or liquid additives corresponding to conventional formulation techniques.

The term "filler" means an organic or inorganic, natural or synthetic component with which the active components are combined to facilitate its application, for example, onto the plants, the seeds, or the soil. The filler can be solid, such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates. The solid fillers which are suitable for granules include natural, crushed or broken rocks, such as calcite, marble, pumice, sepiolite and dolomite; synthetic granules of inorganic or organic flours; granules of organic material such as sawdust, coconut shell, corn car or envelope, or tobacco stem; kieselguhr, tricalcium phosphate, powdered cork or adsorbent carbon black; water-soluble polymers, resins, waxes; or solid fertilizers. Such fillers can be combined with one or more compatible agents such as wetting agents, dispersing agents, emulsifiers or colorings which, when they are solid, can also act as diluents.

The fillers can also be liquid, such as water; alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulfoxide, N,N-dimethylacetamide or N-methylpyrrolidone; N-octylpyrrolidone, liquefied gases; or the like, whether they are taken separately or as a mixture.

The surfactant can be an emulsifier, a dispersing agent or a wetting agent, of ionic or nonionic type, or a mixture of these surfactants. Examples of surfactants include polyacrylic acid salts, lignosulfonic acid salts, phenolsulfonic or naphthalenesulfonic acid salts, polycondensates of ethylene oxide with fatty alcohols or fatty acids or fatty esters or fatty amines, substituted phenols (in particular alkylphenols or arylphenols), ester-salts of sulfosuccinic acid, taurine derivatives (in particular alkyl taurates), phosphoric esters of alcohols or of polycondensates of ethylene oxide with phenols, fatty acid esters with polyols, or sulfate, sulfonate or phosphate functional derivatives of the compounds described above. The presence of at least one surfactant is generally useful when the active agents and/or the inert filler are insoluble or only sparingly soluble in water and when the filler for the said composition to be applied is water.

The agricultural compositions can also contain other additives such as adhesives or colorings. Adhesives such as carboxymethylcellulose, or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be included in the compositions. It is possible to use colorings such as inorganic pigments, such as, for example: iron oxides, titanium oxides, Prussian blue; organic coloring-stuffs, such as those of the alizarin, azo or metal phthalocyanin type; or of trace elements such as iron, manganese, boron, copper, cobalt, molybdenum or zinc salts.

In addition to the active agents and inert carrier, the agricultural compositions of the invention may include agents that have pesticidal properties (in particular, insecticidal, acaricidal or nematocidal properties) or which have properties of regulating plant growth. The compositions may thus include insecticides, acaricides, nematicides, anti-helminths or anti-coccidoses, bactericides, attractant or repellent agents, deodorizers, flavorings or colorings.

The agricultural compositions preferably contain from about 0.1% to about 99% of the active ingredients, more preferably from about 0.5 to about 95% of the active agents. Such amounts may be included in a concentrated composition intended to be diluted prior to administration or may be included in a dilute composition ready to be administered to the crops to be treated.

The effective working doses of the active agents applied vary within wide proportions and depend on several factors, such as the type of microorganism to be treated, the type or level of development of the infested plant, the density of vegetation, and/or the method of application.

Examples of microorganisms that can be treated with the antimicrobial diferulates and the agricultural compositions described herein include bacteria, fungi, oomycetes, or any other microorganism comprising a glucan-containing cell wall.

Pathogenic microorganisms of plants that may be controlled by the antimicrobial diferulates of the invention include microorganisms from the group of oomycetes, including microorganisms from the family of Peronosporaceae, such as *Plasmopara viticola* (vine downy mildew), *Plasmopara halstedei* (sunflower mildew), *Pseudoperonospora* sp. (in particular cucurbit mildew (*Pseudoperonospora cubensis*) and downy mildew of hops (*Pseudoperonospora humuli*)), *Bremia lactucae* (mildew of lettuce), *Peronospora tabacinae* (downy mildew of tobacco), *Peronospora destructor* (downy mildew of onion), *Peronospora parasitica* (downy mildew of cabbage), *Peronospora farinosa* (downy mildew of chicory and downy mildew of beetroot); and microorganisms of the genus *Phytophthora* such as *Phytophthora phaseoli, Phytophthora citrophthora, Phytophthora capsici, Phytophthora cactorum, Phytophthora palmivora, Phytophthora cinnamoni, Phytophthora sojae, Phytophthora megasperma, Phytophthora parasitica, Phytophthora fragariae, Phytophthora cryptogea, Phytophthora porri, Phytophthora nicotianae, Phytophthora infestans* (mildew of Solanaceae, in particular late blight of potato or tomato); among others.

Pathogenic fungi of plants and the associated diseases that may be controlled by the antimicrobial diferulates of the invention include fungi from the group of adelomycetes (ascomycetes), including fungi of the genus *Alternaria*, for example *Alternaria solani* (early blight of Solanaceae and in particular of tomato and potato); fungi of the genus *Guignardia*, in particular *Guignardia bidwelli* (black rot of grapevine); fungi of the genus *Venturia*, for example *Venturia inaequalis, Venturia pirina* (apple or pear scabs); fungi of the genus Oidium, for example oidium of leguminous crops; fungi of the genus *Uncinula*, for example *Uncinula necator* (powdery mildew of grapevine); fungi of the genus *Erysiphe*, for example *Erysiphe polygoni* (powdery mildew of Cruciferac), *Erysiphe cichoracearum, Erysiphe communis* (powdery mildew of beetroot and cabbage), *Erysiphe pisi* (powdery mildew of pea and lucerne), *Erysiphe polyphaga* (powdery mildew of haricot bean and cucumber), *Erysiphe umbelliferarum* (powdery mildew of ombellifera, in particular of carrot); fungi of the genus *Sphaerotheca*, for example *Sphaerotheca fuligena* (powdery mildew of cucurbits, of composites and of tomato) and *Sphaerotheca humuli* (hop mildew); fungi of the genus *Leveillula*, including *Leveillula taurica*; fungi of the genus *Taphrina*, for example *Taphrina deformans* (peach leaf curl); fungi of the genus *Septoria*, for example *Septoria nodorum* and *Septoria tritici* (*Septoria* disease of cercals); fungi of the genus *Sclerotinia*, for example *Sclerotinia sclerotinium*; fungi of the genus *Pseudocercosporella*, for example *P. herpotrichoides* (eyespot of cereals); fungi of the genus *Botrytis*, for example *Botrytis cinerea* (grapevine, vegetable and market garden crops, pea and the like); fungi of the genus *Phomopsis*, for example, *Phomopsis viticola* (excoriosis of grapevine); fungi of the genus *Pyrenospora*; fungi of the genus *Helminthosporium*, for example *Helminthosporium tritici* repentis (yellow leaf spot of wheat) and *Helminthosporium teres* (yellow leaf spot of barley); fungi of the genus *Drechslera* or *Pyrenophora*; fungi of the group of basidiomycetes; fungi of the genus *Puccinia*, for example *Puccinia recondita* or *striiformis* (wheat rust), *Puccinia* triticina, *Puccinia hordei*; and fungi of the family *Rhizoctonia* spp., for example *Rhizoctonia solani*.

In addition to the fungicidal activities, the antimicrobial diferulates and agricultural compositions comprising them may also have biocidal activity against bacteria, such as for example, *Erwinia amylovora* (fire blight), *Xanthomonas campestris* (bacterial streak of stone fruit trees), *Pseudomonas syringae* (pear blossom blight), and bacteria associated with the bacteriosis of rice and cereals.

The plants to which the antimicrobial diferulates and agricultural compositions comprising the antimicrobial diferulates can be administered include grapevine, cereals (wheat, barley, maize, rice), vegetables (haricot bean, onion, cucurbitaceae, cabbage, potato, tomato, sweet pepper, spinach, pea, lettuce, celery, chicory), fruits (strawberry plants, raspberry plants), trees (apple trees, pear trees, cherry trees, ginseng, lemon trees, coconut palms, pecan trees, cacao trees, walnut trees, rubber trees, olive trees, poplars, banana trees), sunflower, beetroot, tobacco, hops, turf, wood, ornamental plants, and horticultural plants, among others.

Various diseases of specific plants that can be treated or prevented with the antimicrobial diferulates and agricultural compositions comprising the antimicrobial diferulates include, for grapevine, downy mildew (*Plasmopara viticola*), powdery mildew (*Uncinula necator*), grey mould (*Botrytis cinerea*), excoriosis (*Phomopsis viticola*), and black rot (*Guignardia bidwelli*); for solanaceae, blight (*Phytophthora infestans*), alternara disease (*Alternaria solani*), and grey mould (*Botrytis cinerea*); for vegetable crops, downy mildew (*Peronospora* sp., *Bremia lactucae, Pseudoperonospora* sp.), alternara (*Alternaria* sp.), sclerotinia disease (*Sclerotinia* sp.), grey mould (*Botrytis cinerea*), foot or root rot (*Rhizoctonia* spp.), powdery mildew (*Erysiphe* sp. and *Sphaerotheca fuliginea*); for arboriculture plants, scab (*Venturia inaequalis, V. pirina*), bacterial diseases (*Erwinia amylovora, Xanthomonas campestris, Pseudomonas syringae*), powdery mildew (*Podosphaera leucotricha*), and monilia (*Monilia fructigena*); for citrus plants scab (*Elsinoe fawcetti*), melanose (*Phomopsis citri*) and *Phytophthora* sp. diseases; for wheat, fusarium diseases (*Microdochium nivale* and *Fusarium roseum*), smuts (*Tilletia caries, Tilletia controversa*, and *Tilletia indica*), septoria disease (*Septoria nodorum*), eyespot (*Pseudocercosporella herpotrichoides*), take-all (*Gaeumannomyces graminis*), fusarium disease of the foot (*F. culmorum, F. graminearum*), rhizoctonia disease (*Rhizoctonia cerealis*), powdery mildew (*Erysiphe graminis*), rusts (*Puccinia striiformis* and *Puccinia recondita*), Septoria diseases (*Septoria tritici* and *Septoria nodorum*), and yellow leaf spot of wheat (*Helminthosporium tritici-vulgaris*); for barley, yellow leaf spot (*Pyrenophora graminea, Bipolaris, Pyrenophora teres*, and *Cochliobolus sativus*), loose smut (*Ustilago nuda*), *fusarium* diseases (*Microdochium nivale* and *Fusarium roseum*), eyespot (*Pseudocercosporella herpotrichoides*), yellow leaf spot (*Pyrenophora teres* and *Cochliobolus sativus*), powdery mildew (*Erysiphe graminis*), dwarf leaf rust (*Puccinia hordei*) and leaf blotch (Rhynchosporium secalis); for potato, tuber diseases (*Helminthosporium solani, Phoma tuberosa, Rhizoctonia solani, Fusarium solani*); for cotton, damping-off diseases and collar rot (*Rhizoctonia solani, Fusarium oxysporum*), black root rot (*Thielaviopsis basicola*); for peas, anthracnose (*Ascochyta pisi, Mycosphaerella pinodes*), fusarium disease (*Fusarium oxysporum*), grey mold (*Botrytis cinerea*), rust (*Uromyces pisi*); for rape plant, grey mould (*Botrytis cinerea*) and sclerotinia disease (*Sclerotinia sclerotinium*); for maize, seed diseases (*Rhizopus* sp., *Penicillium* sp., *Trichoderma* sp., *Aspergillus* sp. and *Gibberella fujikuroi*), yellow leaf spot (*Bipolaris*), fusarium disease (*Fusarium oxysporum*); for rice, foot and root rot (*Rhizoctonia* spp.); for flax, seed diseases (*Alternaria linicola*); for banana, cercospora disease (*Mycosphaerella figiensis*); for turf, rust, powdery mildew, yellow leaf spot, terruric diseases (*Microdochium nivale, Pythium* sp., *Rhizoctonia solani, Sclerotinia homeocarpa*); and for forest trees, damping-off (*Fusarium oxysporum, Rhizoctonia solani*).

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Summary

A rise in resistance to current antifungals necessitates strategies to identify alternative sources of effective fungicides. We report the discovery of poacic acid, a potent antifungal compound found in lignocellulosic hydrolysates of grasses. Chemical genomics using *Saccharomyces cerevisiae* showed that loss of cell wall synthesis and maintenance genes conferred increased sensitivity to poacic acid. Morphological analysis revealed that cells treated with poacic acid behaved similarly to cells treated with other cell wall-targeting drugs and mutants with deletions in genes involved in processes related to cell wall biogenesis. Poacic acid causes rapid cell lysis and is synergistic with caspofungin and fluconazole. The cellular target was identified; poacic acid localized to the cell wall and inhibited β-1,3-glucan synthesis in vivo and in vitro, apparently by directly binding β-1,3-glucan. Through its activity on the glucan layer, poacic acid inhibits growth of the fungi *Sclerotinia sclerotiorum* and *Alternaria solani* as well as the oomycete *Phytophthora sojae*. A single application of poacic acid to leaves infected with the broad range fungal pathogen *S. sclerotiorum* substantially reduced lesion development. The discovery of poacic acid as a antifungal agent targeting β-1,3-glucan highlights the potential side use of products generated in the processing of renewable biomass toward biofuels as a source of valuable bioactive compounds and further clarifies the nature and mechanism of fermentation inhibitors found in lignocellulosic hydrolysates.

BACKGROUND

Lignocellulosics are a potential sugar feedstock for biofuels and bio-based chemicals. Before plant materials can be converted to biofuels by fermentation, their cell wall polysaccharides must be hydrolyzed to sugar monomers for microbial conversion (Sun et al. 2002). The hydrolysis process generates, in addition to the sugars, small acids, furans, and other compounds that affect microbial growth and inhibit fermentation (Piotrowski et al. 2014, Palmqvist et al. 2000, Kkerker et al. 3013, FitzPatrick et al. 2010). The inhibitory effects of these compounds represent a challenge to efficient microbial bioconversion. The primary focus of lignocellulosic-derived inhibitor research has been to understand, evolve, and engineer tolerance in fermentative microbes (Piotrowski et al. 2014). However, as antimicrobial agents, lignocellulosic fermentation inhibitors offer an untapped reservoir of bioactive compounds.

One increasingly important potential use of these inhibitors is as antifungal agents. Worldwide, fungicide-resistant pathogens pose a threat to agricultural sustainability. Pathogen resistance to conventional fungicides affects multiple crops (Avenot et al. 2008, Leroch et al. 2011). Copper-based fungicides are effective in organic agriculture but facing restrictions because of copper accumulation in soils (Wightwick et al. 2013, Mackie et al. 2013). Furthermore, climate change is altering the global distribution of fungal pathogens (Altizer et al. 2013, Garrett et al. 2006). New sources of fungicides are a necessity to keep pace with the evolution of resistant strains and emerging pathogens (Alexander et al. 1997).

The antifungal activities of many of the inhibitors (e.g., ferulic acid and furfural) in hydrolysates have been described (Sarma et al. 2003, Heer et al. 2008), but new compounds continue to be discovered (Jayakody et al. 2011). One under-studied class of compounds derived from grasses and their hydrolysates is the dehydrodiferulates and compounds derived from them (hereafter all simply termed diferulates) (Ralph et al. 1994, Ralph et al. 1998). Diferulates are generated during the hydrolysis of biomass (Ralph et al. 1994, Vismch et al. 2013, Bunzel et al. 2001). At present, the structures of a range of diferulates have been described (Ralph et al. 1994, Vismch et al. 2013), but activities of isolated diferulates have not been explored.

We screened a collection of diferulates found in lignocellulosic hydrolysates for antifungal activity using the yeast *Saccharomyces cerevisiae* as a discovery system for antifungal agents. We focused on the diferulate 8-5-DC (Ralph et al. 1994) derived during hydrolysis from a major diferulate in grasses; we name this compound here as poacic acid, because it is found primarily in grasses (Poaceac). By applying both chemical genomics and morphological analysis, we predicted and confirmed that poacic acid binds to cell wall β-1,3-glucan. We showed its biological activity against not only yeast but also, the economically important fungal and oomycete pathogens *Sclerotinia sclerotiorum, Alternaria solani*, and *Phytophthora sojae.*

Methods

Synthesis of 8-5-DC (Poacic Acid)

To synthesize ethyl ferulate, 700 g ferulic acid was added to a 5 L flask containing 2.5 L absolute ethanol (200 proof), and then 125 mL acetyl chloride was added slowly through a funnel. The reaction mixture was kept stirring for 2 days. After the reaction finished, the solution was concentrated with a rotary evaporator under reducing pressure into viscous oil. The ethyl ferulate product was recrystallized from ethyl acetate-hexanes to give light yellow needle crystal in 92% yield.

To synthesize 8-5-C ethyl diferulate, 88 g ethyl ferulate was dissolved in 1.8 L acetone in in 10 L plastic beaker, and the solution was diluted to 7 L by water. Then 20.5 g urea-$H_2O_2$ complex dissolved in 150 ml water was added, followed by adding 40 mg horse reddish peroxidase (HRP) dissolved in 100 ml water. The white precipitate products formed immediately. The solution was diluted to 10 L by adding water and stirred for 35 mins. Then 40 mL 6 N HCl was added. The product mixtures were blown with compressed air overnight to remove acetone. The crude 8-5-C ethyl diferulate products were recovered by filtration with a glass Buchner filtering funnel (coarse frit). The crude products were air dried in hood and the yield was 91%.

To synthesize 8-5-DC, 120 g NaOH were dissolved in 7.2 L water. To this NaOH solution were added 200 g crude 8-5-C ethyl diferulate while stirring. After dissolution of the diferulate in about 30 mins, the brown color solution was transferred to four 2 L hydrolysis bottles with screw-tied cap. The bottles containing ethyl diferulate solution were kept in a 90° C. oven for 20 h for hydrolysis to produce the 8-5-DC diferulic acid. Then the product solution was cooled down in an ice-water bath to about 10° C. The hydrolysis products were precipitated out by adding 600 mL 6N HCl with stirring for 30 mins. After standing for 20 h, the hydrolysis products were recovered by filtration. The air-dried products were obtained in 81%. The 20 g crude products were loaded in a silica Biotage snap column (340 g silica) and eluted with mixed solvents (hexane-solvent A, 57%-43%, v/v). The solvent A contains ethyl acetate-ethanol-acetic acid (90/10/1, v/v/v). The pure 8-5-DC product was obtained as yellow powder in 17% yield from crude 8-5-C ethyl diferulate.

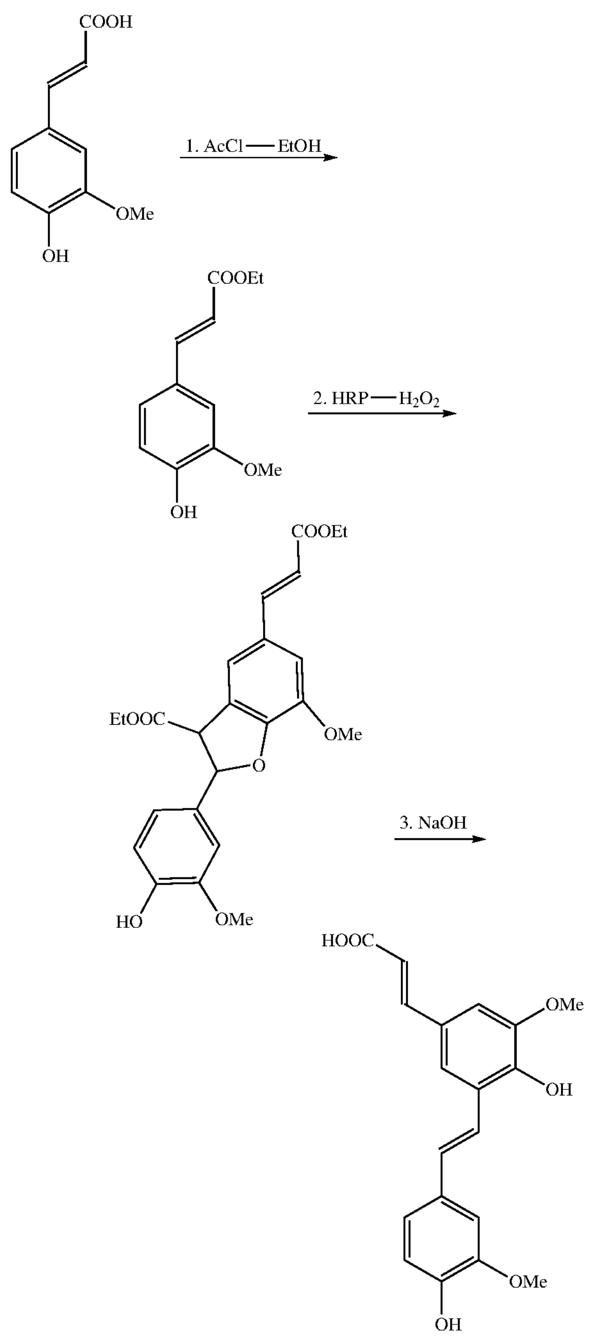

Compounds, Initial Screening, and Growth

The diferulate compounds tested were synthesized as described by Lu et al. (2012) and resuspended in DMSO. Caspofungin, nikkomycin Z, and MMS were purchased from Sigma-Aldrich. Echinocandin B was a gift from O. Kondo (Chugai Pharmaceuticals, Tokyo, Japan). Micafungin was provided by Astellas Pharma. Diferulates were initially screened at a concentration of 1 mg/mL to determine bioactivity. Cells of *Saccharomyces cerevisiae* (MATα pdr1Δ::natMX pdr3Δ::KI.URA3 snq2Δ::KI.LEU2 can1Δ::STE2pr-Sp_his5 lyp1Δ his3Δ1 leu2Δ0 ura3Δ0 met15Δ0), referred to as the control strain, were grown in 200-μL cultures at 30° C. in YPD with a drug or DMSO control. Plates were read on a TECAN M1000 over a 48-h growth period. The specific growth rate was calculated using GCAT analysis software (gcat3-pub.glbrc.org) (Sato et al. 2014). When presented, IC50 values for growth rate inhibition were calculated from triplicate eight-point dose curves and SigmaPlot 12.0. When presented, error bars are means±SEs of at least three replicates.

Chemical Genomic Analysis

Chemical genomic analysis of poacic acid was performed as described previously (Parsons et al. 2006, Fung et al. 2014). The tested yeast deletion collection had ~4,000 strains using the genetic background described by Andrusiak (Andrusiak 2012). The optimal inhibitory concentration of poacic acid for chemical genomic profiling [70-80% growth vs. solvent control in yeast extract-peptone-galactose medium after 24 h of growth] was determined using an eight-point dose curve. A concentration of 88 μg/mL inhibited growth within this range; 200-μL cultures of the pooled deletion collection of *S. cerevisiae* were grown with 88 μg/mL poacic acid (n=3) or a DMSO control in triplicate for 48 h at 30° C. Genomic DNA was extracted using the Epicentre MasterPure Yeast DNA Purification Kit. Mutant-specific molecular barcodes were amplified with specially designed multiplex primers (Smith et al. 2009). The barcodes were sequenced using an Illumina MiSeq. Replicates of each condition, poacic acid (n=3) or DMSO (n=2), were sequenced. The barcode counts for each yeast deletion mutant in the presence of poacic acid were compared to the DMSO control conditions to determine sensitivity or resistance of individual strains (the chemical genetic interaction score) (Parsons et al. 2006). To determine a P value for each top sensitive and resistant mutant, we used the EdgeR package (Robinson et al. 2014, Robinson et al. 2010). A Bonferroni-corrected hypergeometric distribution test was used to search for significant enrichment of GO terms among the top 10 sensitive and resistant deletion mutants (Boyle et al. 2004). To understand the pathways that were most affected by poacic acid, we developed a protein complex/pathway score based on the summation of the z scores for each complex/pathway (Pathway z score). Correlation of the chemical genomic profile of poacic acid with the yeast genetic interaction network was performed as previously described (Costanzo et al. 2010).

Determining the Most Sensitive Pathway Through Chemical Genomics

A complex/pathway score based on chemical genomic data to identify protein complexes or pathways was developed based on which members showed significant deviation in their chemical genetic interactions in the presence of a compound. For each complex, the chemical genetic interaction score of the genes in the complex with the compound was summed. To determine significance, the expectations for such a sum for random sets of genes of equal size were calculated. The random sets of equal size were expected to have means equal to the background mean and SDs equal to the background SD/sqrt(n). With this information, a z score (number of SDs from the expected mean) for each complex or pathway can be computed:

$$\text{Pathway } z\text{-score} = (\Sigma - \mu)/(\sigma \times sqrt(n)),$$

where Σ=sum of the chemical genetic interaction scores of genes in the complex, μ=mean of the chemical genetic interaction scores of the compounds with all genes studies, σ=SD of chemical genetic interaction scores of the compounds with all genes in the study, and n=size of the complex.

Multivariate Morphological Analysis

Cells of budding yeast *S. cerevisiae* (BY4741 his3Δ::KanMX; hereafter, his3Δ) were cultured in 2 mL 1% Bacto yeast extract (BD Biosciences), 2% Bacto peptone (BD Biosciences), and 2% glucose (YPD) with 0, 25, 50, 75, 100, or 125 μg/mL poacic acid or a DMSO control at 25° C. for 16 h until the early log phase. The maximum concentration of the drug (125 μg/mL) was determined based on the growth inhibition rates (10%). Cell fixation, staining, and observation were performed (n=5) as described previously (Ohya et al. 2005). Images of cell shape, actin, and nuclear DNA were analyzed using the image processing software CalMorph (version 1.2), which extracted a total of 501 morphological quantitative values from at least 200 individual cells in each experiment (Ohya et al. 2005). Images were processed using Photoshop CS2 (Adobe Systems) for illustrative purposes.

To assess the morphological similarity between the cells treated with poacic acid and nonessential deletion mutants or cells treated with other cell wall-affecting drugs, their morphological profiles were compared as described previously (Ohnuki et al. 2010). To identify functional gene clusters, the most significant similar mutants (43 genes, P<0.01 after Bonferroni correction, t test) were selected as a query for GO term analysis (GO term finder in the *Saccharomyces* genome database).

To extract independent and characteristic features of morphology induced by poacic acid, a two-step principal component analysis was performed as described previously (Ohnuki et al. 2012). To compare phenotypic noise in the yeast population (poacic acid vs. DMSO), the noise score was calculated as described previously (Yvert et al. 2013).

Measurement of In Vivo β-1,3-Glucan Synthesis

Inhibition of in vivo β-1,3-glucan synthesis was measured as described previously with slight modification (n=3) (Abe et al. 2003). Yeast cells (his3Δ) were grown in YPD to early log phase at 25° C. The cultured cells were diluted to 1×107 cells per 1 mL with 1 mL of YPD medium containing one-tenth the glucose containing 23.125 kBq [14C] glucose (ARC0122; American Radiolabeled Chemicals) and test compounds [250 μg/mL for poacic acid, 4 μg/mL for echinocandin B, 30 mM for hydroxyurea (negative control), or 0.4% (vol/vol) DMSO as a solvent control]. The cells were radiolabeled by culturing at 25° C. for 2 h. The labeled cells were harvested and incubated with 1 N NaOH at 80° C. for 30 min. The insoluble pellets were resuspended in 10 mM Tris. HCl, pH 7.5, containing 5 mg/mL zymolyase 100T (Seikagaku) and incubated at 37° C. for 18 h. After digestion, the zymolyase-resistant material was removed by centrifugation (15,000×g for 15 min), and the zymolyase-degradation product (mostly β-1,3-glucan) was purified by ultrafiltration with a centrifugal filter membrane (Amicon Ultra 0.5 mL; molecular weight cutoff is 10,000; Millipore). The flow-through fraction was mixed with scintillation mixture (Ultima Gold; PerkinElmer), and radioactivity was measured by a scintillation counter (LSC-6100; Aloka). The differences in the incorporation rates in samples were normalized by AOD600 measured before and after the labeling period.

Measurement of β-1,3-Glucan Synthase Activity in the Membrane Fraction

After the membrane fraction was prepared from *S. cerevisiae* BY4741 as described previously (n=3) (Abe et al. 2001), β-1,3-glucan synthase activity was measured as described previously (n=3) (Inoue et al. 1995) with slight modification. Briefly, 20 μL membrane fraction (~70 μg total protein) was added to a reaction mixture (final volume of 100 μL) containing 50 mM Tris. HCl, pH 7.5, 10 mM potassium fluoride, 1 mM EDTA, 0.2 mM UDP-Glc (with 89 Bq UDP-[Glucose-14C]; NEC403; PerkinElmer), and different concentrations of poacic acid (1.25, 2.5, 5, 10, 20, 40, 80, 160, or 320 μg/mL). The reaction mixture was incubated at 25° C. for 30 min and stopped by the addition of ethanol. To trap reaction product (β-1,3-glucan polymer), the reaction mixture was filtered through the membrane filter (mixed cellulose esters; 0.2 μm in pore size; ADVANTEC), washed one time with 2 mL distilled water, and dried at room temperature. After addition of scintillation mixture (Econofluor-2; PerkinElmer), radioactivity was measured by a scintillation counter (LSC-6100; Aloka). Inhibition curves and IC50 values were determined using R software (ver. 3.0.1) by sigmoidal curve fitting with the glm function.

Growth Inhibition of Plant Pathogens

To test inhibition in liquid culture, a dose curve of 0, 125, 250, and 500 μg/mL poacic acid in 100 mL potato dextrose broth (n=3) was used. Cultures of *S. sclerotiorum* strain 1980 were inoculated with 100 μL homogenized mycelia and grown at 25° C. for 48 h. The mycelia in the liquid media were dried and weighed. The growth inhibition of poacic acid on solid agar cultures (potato dextrose agar) was assessed by generating replicate plates (n=3) containing 0, 125, 250, and 500 μg/mL poacic acid. Plates were inoculated with an actively growing plug of *S. sclerotiorum* and grown at 25° C. The mycelial radial growth after 48 h was measured. Inhibition of *S. sclerotiorum* in planta was tested by inoculating detached soybean leaves of the commercial variety Williams 82 with an agar plug of actively growing *S. sclerotiorum* mycelia. Leaves were treated one time before inoculation with either an aerosol spray of water with DMSO (control) or a 500 μg/mL solution of poacic acid. Leaves were incubated in a moist environment, and lesion development was monitored up to 120 h postinoculation. Field strains of *P. sojae* and *A. solani* were grown on cornmeal and potato dextrose agar plates, respectively, at room temperature for 7 and 5 d, respectively, before measurement. The growth inhibition of poacic acid was assessed at 0, 500, 1,000, and 1,500 μg/mL in replicate plates (n=3). Agar plugs from actively growing cultures were placed at the center of the plates and allowed to grow at room temperature. Colony diameter was monitored for each treatment in a time-course experiment. One-way ANOVA and Tukey's test were used to calculate the differences between drug treatments among treatments.

Isolation, Sequencing, and Evaluation of Drug-Resistant Mutants

Agar containing 500 μg/mL poacic acid was inoculated with ~1 million cells of yeast (control strain). After 1 wk, two colonies were found growing on the agar. Single-colony isolates were obtained and found to be resistant to poacic acid. For whole-genome sequencing, single-colony isolates of poacic acid-resistant mutant, the caspofungin-resistant mutant, and the control strain (WT) were grown in triplicate 200-μL cultures and pooled for genomic DNA extraction (Epicentre MasterPure Yeast Kit; MPY80200). The genomic DNA was prepared for Illumina whole-genome sequencing using the Illumina TruSeqKkit (FC-121-3001) and sequenced by 150-bp paired-end reads on the MiSeq platform.

To determine mutations in the drug-resistant mutants, read quality analysis was performed using FastQC (bioinformatics.babraham.ac.uk). Short reads were examined for quality and trimmed at the 3' end when average base quality in a 3-nt window fell below Q30. Short reads were mapped to the standard *S. cerevisiae* reference genome, strain S288c (obtained from the National Center for Biotechnology Information RefSeq repository), using Burrows-Wheeler Alignment (BWA version 0.6.2) (Li et al. 2009) using the default parameters, with the exception of the fraction of missing alignments threshold, which was set at 0.08 (−n in bwa aln). SNP and indel detection were performed with the Genome Analysis Toolkit (GATK version 1.4) (DePristo et al. 2011) following their best practice variant-calling workflow (broadinstitute.org). Duplicate reads were marked followed by base quality recalibration using a single nucleotide polymorphism database designed for *S. cerevisiae*. To minimize false-positive variant calls, stringent parameters were used: namely, the minimum base quality required to consider a base for calling was 30, and the minimum phred-scaled confidence threshold for genotype calling was 50 (−mbq and −scc in the UnifiedGenotyper tool). Custom Perl scripts were used to further filter calls on the basis of read depth, mapping quality, and strand bias. This analysis revealed an SNP in the gene SUR1 (glutamate>stop codon) in the poacic acid-resistant mutant.

Cell Leakage Assays

A FungaLight Cell Viability Assay (L34952; Invitrogen) using a Guava Flow Cytometer (Millipore) was used to determine if poacic acid caused membrane damage. The population of stained cells (damaged integrity) vs. non-stained cells can be determined by flow cytometry. Caspofungin (50 ng/mL) was included as a positive control. MMS and DMSO were included as a noncell wall-targeting control and a solvent control, respectively. To test the effects of the compounds on both active and arrested cells, log-phase cultures were washed with 1×PBS and resuspended to an OD0.5 in either YPD medium or YP (no carbon source) in the presence of the drugs (n=3) for 4 h at 30° C. The cells were then stained and immediately read by flow cytometry. One-way ANOVA and Tukey's test were used to calculate the difference between drug treatments among cells with arrested growth.

Synergy Screening

To test for synergy, a 6×6-dose matrix was initially used to identify potentially synergistic dose combinations, and these points were then confirmed in triplicate. Cultures (200 µL) were grown with combinations of poacic acid (125 µg/mL), caspofungin (12.5 ng/mL), and fluconazole (3.8 µg/mL), and the ODs of relevant single-agent and solvent controls were measured after 24 h. Synergy was determined by comparing actual OD in the presence of compound combinations with an expected value calculated using the multiplicative hypothesis. This method assumes that, in the absence of an interaction, each compound would decrease the OD of the cell culture by the same fraction in the presence of the other compound as it does when applied alone (that is, $E=A\times B/C$, where E is the expected OD, A is OD when compound A is applied alone, B is OD when compound B is applied alone, and C is OD of the control culture (DMSO). In the presence of synergy, the actual OD value is lower than the expected OD. A paired t test was used to confirm statistical significance of this difference in three replicates of the experiment.

Staining of Cells with Poacic Acid

Log-phase yeast cells (his34) were harvested by centrifugation, washed two times with PBS, sonicated mildly, and then, incubated with 0.25% (wt/vol) poacic acid for 5 min. A small aliquot of the cells was mounted on a glass slide and observed under an Axioimager MI Fluorescence Microscope (Carl Zeiss) using the XF09 Filter Set (Opto Science; excitation wavelength, 340-390 nm; emission wavelength, 517.5-552.5 nm).

Mannoprotein and Glucan Staining

β-1,3-Glucan was stained with aniline blue (016-21302; Wako Chemicals) as described previously (Watanabe et al. 2001) with slight modification. Briefly, log-phase yeast cells (his3A) were cultured in YPD with poacic acid (125 µg/mL) at 25° C. Then, cells were collected at 0, 2, 4, and 6 h after treatment and stained with aniline blue without fixation as described previously (Okada et al. 2015). Cells mounted on a glass slide were exposed to UV for 30 s to bleach out poacic acid fluorescence before acquiring images. Staining of chitin or mannoproteins with calcofluor white (F3543; Sigma-Aldrich) or Alexa594-ConA (C11253; Life Technologies), respectively, was performed as described previously (Okada et al. 2015). For cell-free glucan staining, yeast glucan (G0331; Tokyo Chemical Industry) was suspended to 0.125% (wt/vol) poacic acid and observed under a fluorescent microscope using a regular DAPI filter set (Carl Zeiss).

Determination of Ferulate and Diferulates by Reverse-Phase HPLC-High-Resolution/Accurate MS in Hydrolysates Ammonia fiber expansion treated corn stover hydrolysates samples were diluted 1:10, and 20-µL samples were analyzed by reverse-phase (C18) HPLC-high-resolution/accurate MS. Peak areas of peaks matching in retention time and accurate mass±10 ppm of authentic reference standards were used to calculate concentrations by comparison with an external standard curve.

Results

Diferulates with Antifungal Activity

Figure 2:
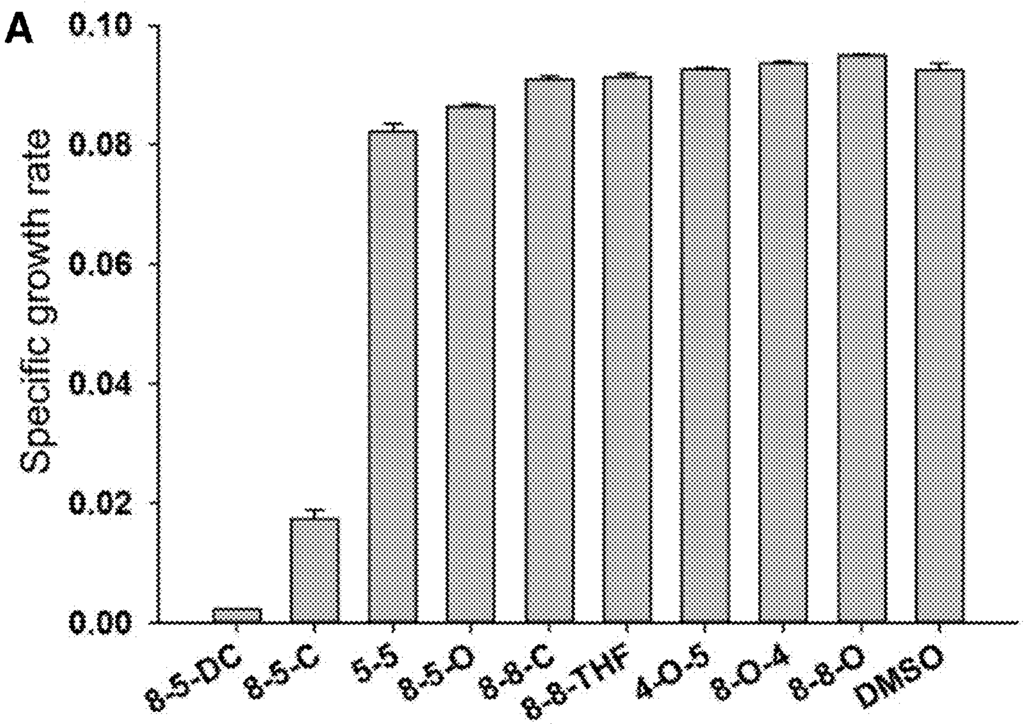
FIG. 2. Bioactivity of diferulates. The bioactivity of nine diferulates against *S. cerevisiae* at 1 mg/mL was tested. Poacic acid (8-5-DC) had (A) the highest bioactivity and (B) an IC50 of 111 μg/mL (mean+SE).
Figure 2:
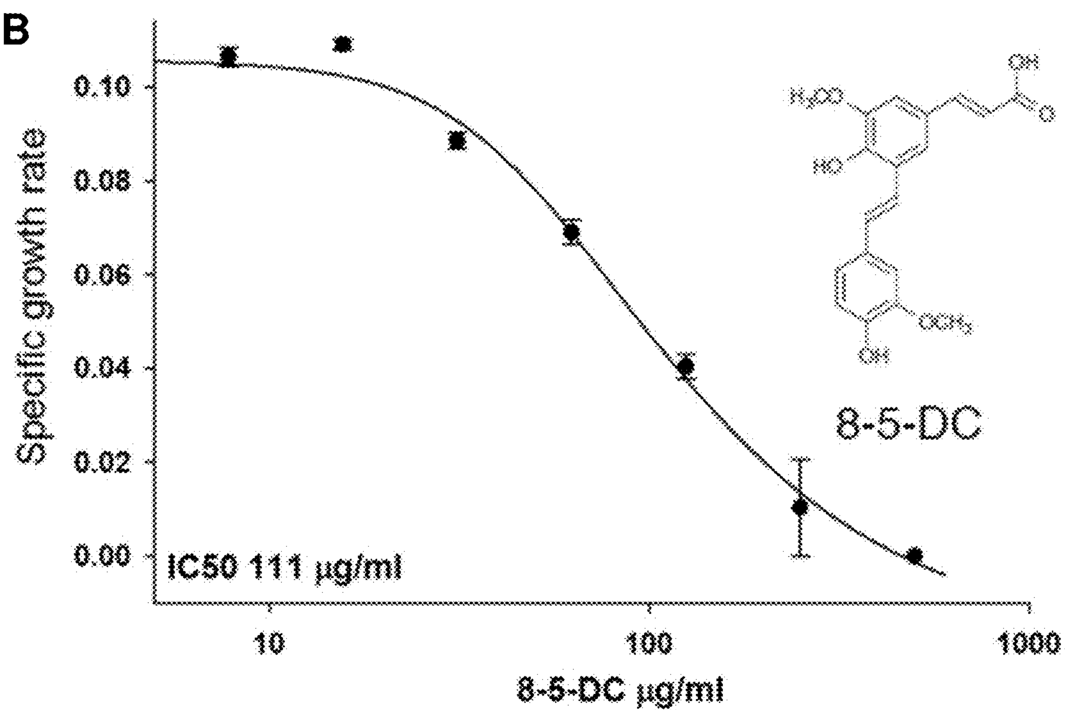

We tested a collection of nine diferulates known to occur in hydrolysates from corn stover (FIGS. 1A-1I and Table 1) for their effects on *S. cerevisiae* growth (FIG. 2). Of these, only two had detectable bioactivity at the tested concentration of 1 mg/mL (FIG. 2, panel A). In particular, poacic acid had the greatest antifungal activity, with an IC50 of 111 µg/mL (324 µM) against our control yeast (FIG. 2, panel B). This inhibition is comparable with that of the widely used fungicides picoxystrobin (IC50 of 308 µM) and polyoxin D (IC50 of 340 µM) and substantially lower than that of the primary fungicide used in organic agriculture, copper sulfate (IC50 of 2.4 mM) (23-25).

TABLE 1

Nomenclature, molecular weight, and IUPAC names of diferulate derivatives tested.

| Name | Description | Molecular Weight | IUPAC |
|---|---|---|---|
| 8-8-C | 8-8-coupled cyclic diferulic acid | 386 | trans-7-Hydroxy-1-(4-hydroxy-3-methoxyphenyl)-6-methoxy-1,2-dihydronaphthalene-2,3-dicarboxylic acid |
| 4-O-5 | 4-O-5-coupled diferulic acid | 386 | (E)-3-{4-[(E)-2-Carboxyvinyl]-2-methoxyphenoxy}-4-hydroxy-5-methoxycinnamic acid |
| 8-5-C | 8-5-coupled cyclic diferulic acid | 386 | trans-5-[(E)-2-carboxyvinyl]-2-(4-hydroxy-3-methoxyphenyl)-7-methoxy-2,3-dihydrobenzofuran-3-carboxylic acid |
| 8-8-O | 8-8-coupled opened diferulic acid | 386 | 4,4'-Dihydroxy-5,5'-dimethoxy-8,8'-bicinnamic acid |

TABLE 1-continued

Nomenclature, molecular weight, and IUPAC names of diferulate derivatives tested.

| Name | Description | Molecular Weight | IUPAC |
|---|---|---|---|
| 8-8-THF | 8-8-coupled tetrahydrofuran diferulic acid | 404 | 2,5-bis-(4-Hydroxy-3-methoxyphenyl)-tetrahydrofuran-3,4-dicarboxylic acid |
| 8-0-4 | 8-O-4-coupled diferulic acid | 386 | (Z)-8-{4-[(E)-2-Carboxyvinyl]-2-methoxyphenoxy}-4-hydroxy-3-methoxy-cinnamic acid |
| 5-5 | 5-5-coupled diferulic acid | 386 | (E,E)-4,4'-Dihydroxy-5,5'-dimethoxy-3,3'-bicinnamic acid |
| 8-5-O | 8-5-coupled opened diferulic acid | 386 | (E,E)-4,4'-dihydroxy-3,5'-dimethoxy-8,3'-bicinnamic acid |
| 8-5-DC (poacic acid) | 8-5-coupled decarboxy diferulic acid | 342 | (E)-4-Hydroxy-3-{2-[(E)-4-hydroxy-3-methoxystyryl]}-5-methoxycinnamic acid |

IUPAC, International Union of Pure and Applied Chemistry

Chemical Genomics Predict That Poacic Acid Targets the Fungal Cell Wall

To gain insight into the mode of action and the cellular target of poacic acid, we conducted chemical genomic analysis, a method that uses genome-wide collections of viable gene-deletion mutants to identify genes with deletions that confer sensitivity or resistance to bioactive compounds (Parsons et al. 2006, Ho et al. 2011). The resulting set of sensitive and resistant gene-deletion mutants associated with a response yields functional insight into the mode of action (Parsons et al. 2006). We challenged a pooled mixture of ~4,000 different yeast gene-deletion mutants with either poacic acid or a solvent control (DMSO). Sequencing of strain-specific DNA barcodes enabled us to decipher the relative fitness of each yeast mutant in the presence of the drug relative to the solvent control (Smith et al. 2009).

Figure 3:
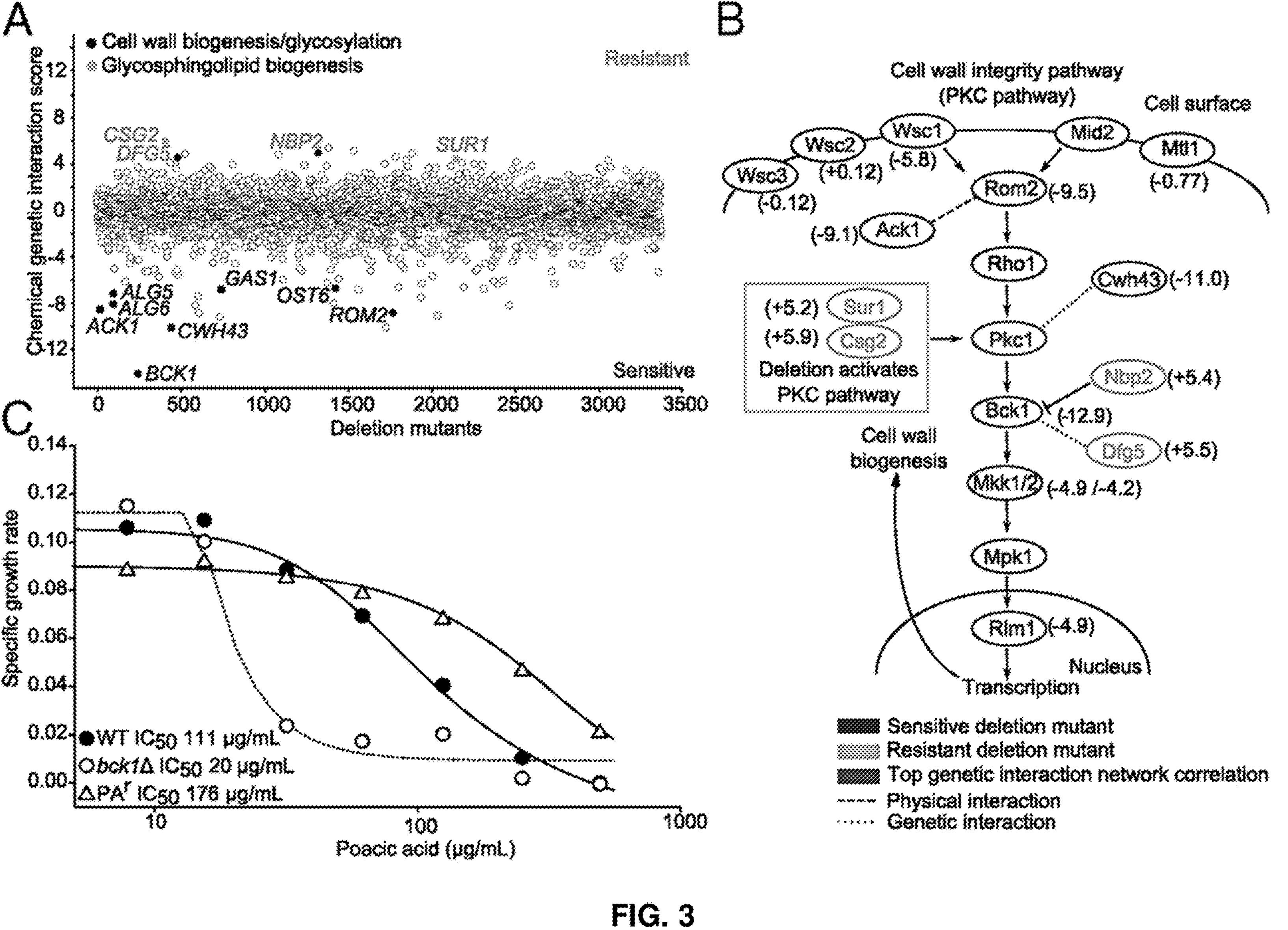
FIG. 3. Chemical genomics of poacic acid. (A) Treatment of the yeast deletion collection with poacic acid revealed that mutants involved in cell wall biosynthesis and glycosylation (DFG5, NBP2, ALG5, ALG6, ACK1, BCK1, CWH43, GAS1, OST6, ROM2) were sensitive and resistant to the compound. Mutants in genes involved in glycosphingolipid biogenesis (CSG2, SUR1) were among the most resistant. (B) The PKC pathway, which governs cell wall integrity signaling, was the most sensitive pathway (Pathway z score=−7.85), with many members and interacting genes showing sensitivity to poacic acid (chemical genetic interaction score in parentheses). Comparison with the yeast genetic interaction network indicated that the genetic interaction profile of the essential gene PKC1 was most significantly correlated to the chemical genomic profile of poacic acid (P<0.001). (C) Mutants of the gene encoding the cell wall signaling kinase BCK1 were six-fold more sensitive to poacic acid, whereas a poacic acid-resistant mutant (PAr) with an SNP in SUR1 had increased resistance compared with the control strain (mean and SE bars were removed for clarity).

Deletion mutants for genes involved in cell wall and glycosylation-related processes were present in the top significantly sensitive and resistant strains (FIG. 3, panel A, and Table 2). Among the top 10 deletion mutants sensitive to poacic acid, we detected enrichment for genes involved in the gene ontology (GO) category fungal-type cell wall organization ($P<0.01$). These mutants included deletion alleles of BCK1 (bypass of C kinase), which encodes an MAPKKK in the Pkc1p (protein kinase C) cell wall integrity signaling pathway (PKC pathway); CWH43, which encodes a membrane protein involved in cell wall biogenesis and its null mutation is synthetically lethal with PKC1 mutants (Martin-Yken et al. 2001); ROM2 (Rho1 multicopy suppressor), a GDP/GTP exchange factor for Rho1p and another component of the PKC pathway; and ACK1, which seems to encode an upstream activator of Pkc1p and has a physical interaction with Rom2p. Overall, the PKC pathway was the most sensitive pathway to poacic acid (Pathway z score=−7.85) (FIG. 3, panel B). This profile is similar to the chemical genomic profiles of other agents that target the cell wall and related processes (e.g., caspofungin) (Parsons et al. 2006). Deletion mutants of BCK1 are hypersensitive to agents that compromise glycosylation (tunicamycin) and cell wall β-1,3-glucan biosynthesis (caspofungin) (Parsons et al. 2006). We confirmed the sensitivity of the individual bck1Δ mutant and found a six-fold reduction in the IC50 against poacic acid compared with the control strain (WT) (FIG. 3, panel C).

TABLE 2

Top 10 sensitive and resistant deletion mutants among the poacic acid-treated deletion collection.*

| Gene | Z Score | P adjusted |
|---|---|---|
| Sensitive mutants | | |
| BCK1 −12.91 2.58E | 28 | BCK1 −12.91 2.58E |
| CWH43 −10.99 7.98E | 7 | CWH43 −10.99 7.98E |
| RGD1 −10.16 1.21E | 7 | RGD1 −10.16 1.21E |
| ROM2 −9.47 8.88E | 8 | ROM2 −9.47 8.88E |
| FYV8 −9.11 1.11E | 14 | FYV8 −9.11 1.11E |
| ACK1 −9.09 1.39E | 5 | ACK1 −9.09 1.39E |
| ALG6 −8.30 1.82E | 11 | ALG6 −8.30 1.82E |
| EMC4 −7.92 1.90E | 3 | EMC4 −7.92 1.90E |
| SNG1 −7.91 8.96E | 13 | SNG1 −7.91 8.96E |
| ERG2 −7.80 4.76E | 3 | ERG2 −7.80 4.76E |
| Resistant mutants | | |
| CSG2 5.89 1.57E | 3 | CSG2 5.89 1.57E |
| LCL1 5.79 4.51E | 3 | LCL1 5.79 4.51E |
| DFG5 5.51 1.34E | 2 | DFG5 5.51 1.34E |
| NBP2 5.43 1.57E | 3 | NBP2 5.43 1.57E |
| RTS1 5.39 6.26E | 3 | RTS1 5.39 6.26E |
| NUP170 5.33 2.79E | 6 | NUP170 5.33 2.79E |
| DSF2 5.32 6.68E | 5 | DSF2 5.32 6.68E |
| SUR1 5.21 5.34E | 3 | SUR1 5.21 5.34E |
| PIB2 4.96 2.79E | 6 | PIB2 4.96 2.79E |
| RPL21B 4.81 1.11E | 5 | RPL21B 4.81 1.11E |

*See Piotrowski et al. 2015 for descriptions of genes.

Among the top significantly resistant strains, we detected significant enrichment for deletions of genes involved in the GO category glycosphingolipid biosynthetic process ($P<0.01$) driven by csg2Δ (calcium sensitive growth) and sur1Δ (suppressor of Rvs161 and rvs167 mutations) (FIG. 3, panel A, and Table 2). Deletion of glycosphingolipid genes has been shown to activate the PKC pathway and cell wall biogenesis (FIG. 3, panel B) (Jesch et al. 2010). Involvement of SUR1 in poacic acid sensitivity was confirmed when we isolated a spontaneous chain-termination mutant in SUR1 able to form colonies on agar with 500 μg poacic acid/mL (FIG. 3, panel C). Additionally, some other cell wall-related gene mutants were resistant to poacic acid. A deletion mutant of NBP2 (Nap1 binding protein) was resistant to poacic acid (FIG. 3, panel A); Nbp2p down-regulates cell wall biogenesis through an interaction with Bck1p, which is activated by Pkc1p (FIG. 3, panel B) (Ohkuni et al. 2003). Thus, it seems that defects in the PKC pathway confer sensitivity to poacic acid, whereas activation of the PKC pathway confers resistance. A deletion mutant of DFG5 (defective for filamentous growth) also was resistant to poacic acid; DFG5 encodes a GPI-anchored protein involved in cell wall biogenesis that also has a genetic interaction with Bck1p (Kitagaki et al. 2002, urma et al. 2013).

Because the chemical inhibitor of a gene product tends to mimic the loss-of-function phenotype of a mutant that inactivates the gene, the chemical-genomic profile for a bioactive compound can resemble the genetic interaction profile for the target (Costanzo et al. 2010). PKC1 has a genetic interaction profile that is most significantly correlated to the chemical genomic profile of poacic acid (FIG. 3, panel B) ($P<0.0001$). PKC1 is an essential gene required for growth and response to cell wall stress, and it has been implicated as a key mediator of cell wall-targeting drugs, such as the echinocandins (Reinoso-Martin et al. 2003). Together, these data narrowed our target search to the fungal cell wall. Poacic acid could directly damage the cell wall, inhibit a key cell wall synthesis enzyme, or disrupt the PKC pathway.

Morphological Analysis Revealed that Poacic Acid Affects the Fungal Cell Wall

Figure 4:
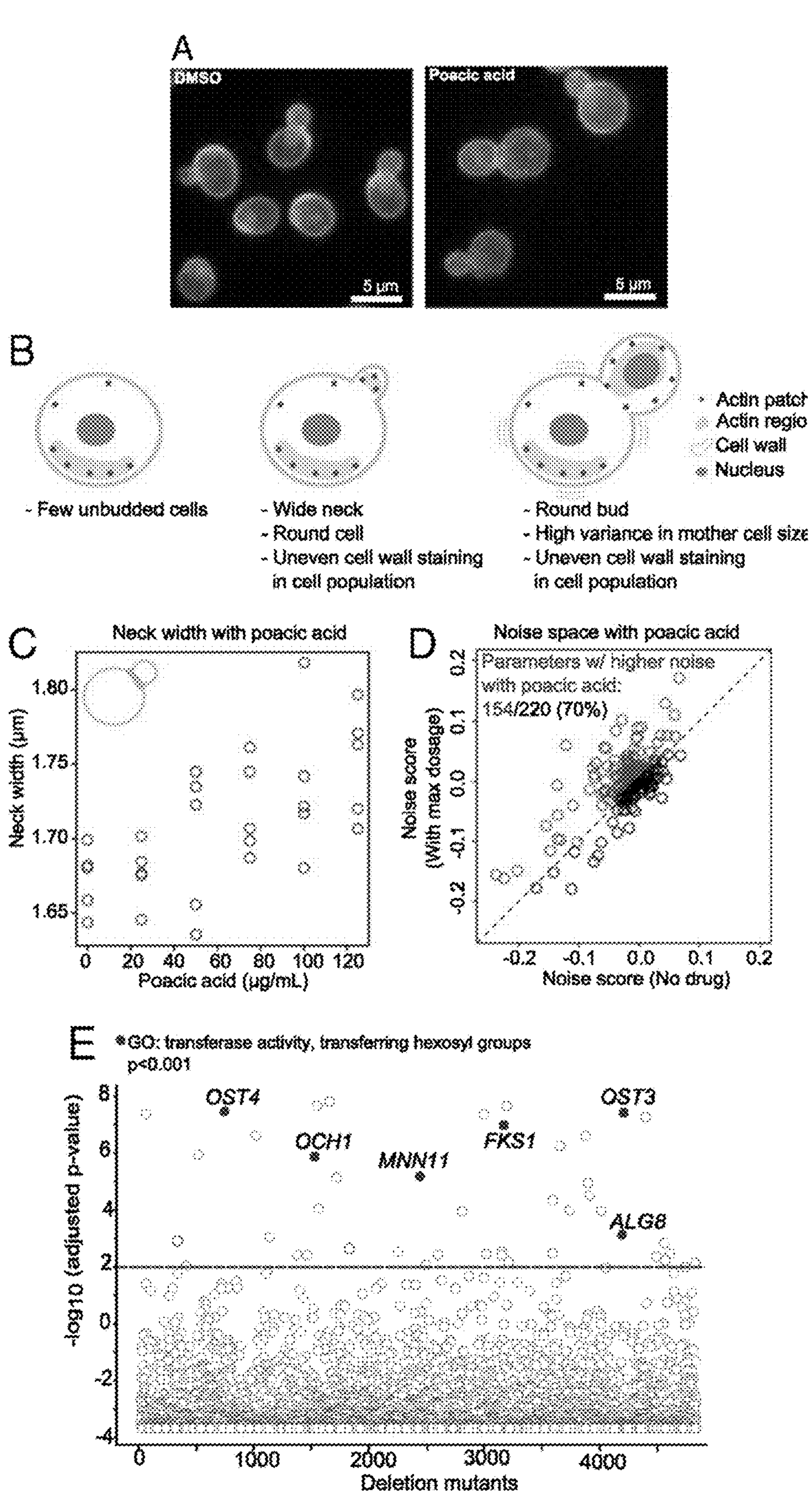
FIG. 4. Morphological characteristics of poacic acid-treated cells. Poacic acid treatment caused (A and B) abnormal cell morphology and (C and D) morphological characteristics similar to those caused by other cell wall-targeting agents. Poacic acid-treated cells had (C) a dose-dependent increased bud neck size and (D) heterogeneity of cell morphology. (E) The phenotype of poacic acid-treated cells was highly correlated with the phenotypes of mutants in genes involved in transferase activity transferring hexosyl groups (P<0.001). The dashed line indicates an adjusted P value of <0.01.

We investigated the morphological changes induced by poacic acid using high-dimensional microscopy (Ohnuki et al. 2010, Ohya et al. 2005). Recently, two morphological features (a wide neck and morphological heterogencity) were reported as common phenotypes in cells treated with agents known to affect the cell wall (Okada et al. 2014). The morphologies of cells exposed to poacic acid had both features (FIG. 4, panels A and B); they displayed dose-dependent increase in bud neck size (FIG. 4, panel C) and heterogeneous morphologies (FIG. 4, panel D). Because mutants displaying a high correlation with a drug phenotype can help identify targeted processes, we next compared the morphology of poacic acid-treated cells with the individual morphologies of 4,718 yeast deletion mutants (Ohya et al. 2005, Ohnuki et al. 2012, Iwaki et al. 2013). Forty-three deletion mutants had morphological profiles statistically similar ($P<0.01$) to those of poacic acid (FIG. 4, panel E, and Table 3). Within the top correlations, we found significant enrichment of genes in the GO category transferase activity, transferring hexosyl groups ($P<0.001$). This GO category contained genes responsible for key processes in the cell wall biogenesis, such as OCH1, which encodes a mannosyltransferase that initiates polymannose outer chain elongation, and FKS1 (FK506 sensitivity), which encodes a catalytic subunit of β-1,3-glucan synthase. Taken together, these data further indicate that poacic acid affects the yeast cell wall, consistent with the chemical genomic analysis.

TABLE 3

Deletion mutants with significant morphological correlations with poacic acid-treated cells.*

| Gene | R value | P with Bonferroni correction |
|---|---|---|
| COG1 | 0.61 | 1.52E−8 |
| NPY1 | 0.61 | 2.08E−8 |
| SUR4 | 0.61 | 2.25E−8 |
| OST4 | 0.61 | 3.31E−8 |
| OST3 | 0.61 | 3.75E−8 |
| YLR111W | 0.60 | 4.20E−8 |
| YAL058C-A | 0.60 | 4.24E−8 |
| SNC2 | 0.60 | 5.53E−8 |
| FKS1 | 0.59 | 1.01E−7 |
| BNI1 | 0.59 | 2.39E−7 |
| SWA2 | 0.59 | 2.41E−7 |
| GAS1 | 0.58 | 5.56E−7 |
| PER1 | 0.57 | 1.14E−6 |
| OCH1 | 0.57 | 1.34E−6 |
| MNN11 | 0.55 | 6.42E−6 |
| CAX4 | 0.55 | 7.14E−6 |
| MON2 | 0.54 | 1.13E−5 |
| KRE1 | 0.53 | 2.30E−5 |
| DFG5 | 0.52 | 4.40E−5 |
| GUP1 | 0.51 | 8.67E−5 |
| TPM1 | 0.51 | 1.02E−4 |
| YOL013W-A | 0.51 | 1.09E−04 |
| RHO4 | 0.51 | 1.10E−4 |
| ALG8 | 0.48 | 7.48E−4 |
| VPS52 | 0.48 | 9.14E−4 |
| GDT1 | 0.47 | 1.26E−3 |
| UME1 | 0.47 | 1.42E−3 |
| CLC1 | 0.46 | 2.19E−3 |
| MMS2 | 0.46 | 2.87E−3 |
| IMP2 | 0.46 | 2.91E−3 |
| PEP5 | 0.46 | 3.17E−3 |
| YPL184C | 0.46 | 3.43E−3 |
| PEP3 | 0.46 | 3.63E−3 |
| CAP1 | 0.45 | 3.76E−3 |
| YFR016C | 0.45 | 3.78E−3 |
| PEA2 | 0.45 | 3.82E−3 |

TABLE 3-continued

Deletion mutants with significant morphological correlations with poacic acid-treated cells.*

| Gene | R value | P with Bonferroni correction |
|---|---|---|
| BUD6 | 0.45 | 3.85E−3 |
| VPS16 | 0.45 | 4.54E−3 |
| POC4 | 0.45 | 5.86E−3 |
| VPS33 | 0.45 | 6.49E−3 |
| OPT2 | 0.44 | 7.41E−3 |
| BNA1 | 0.44 | 8.62E−3 |
| PPS1 | 0.44 | 8.99E−3 |

*See Piotrowski et al. 2015 for descriptions of genes.

Figure 5:
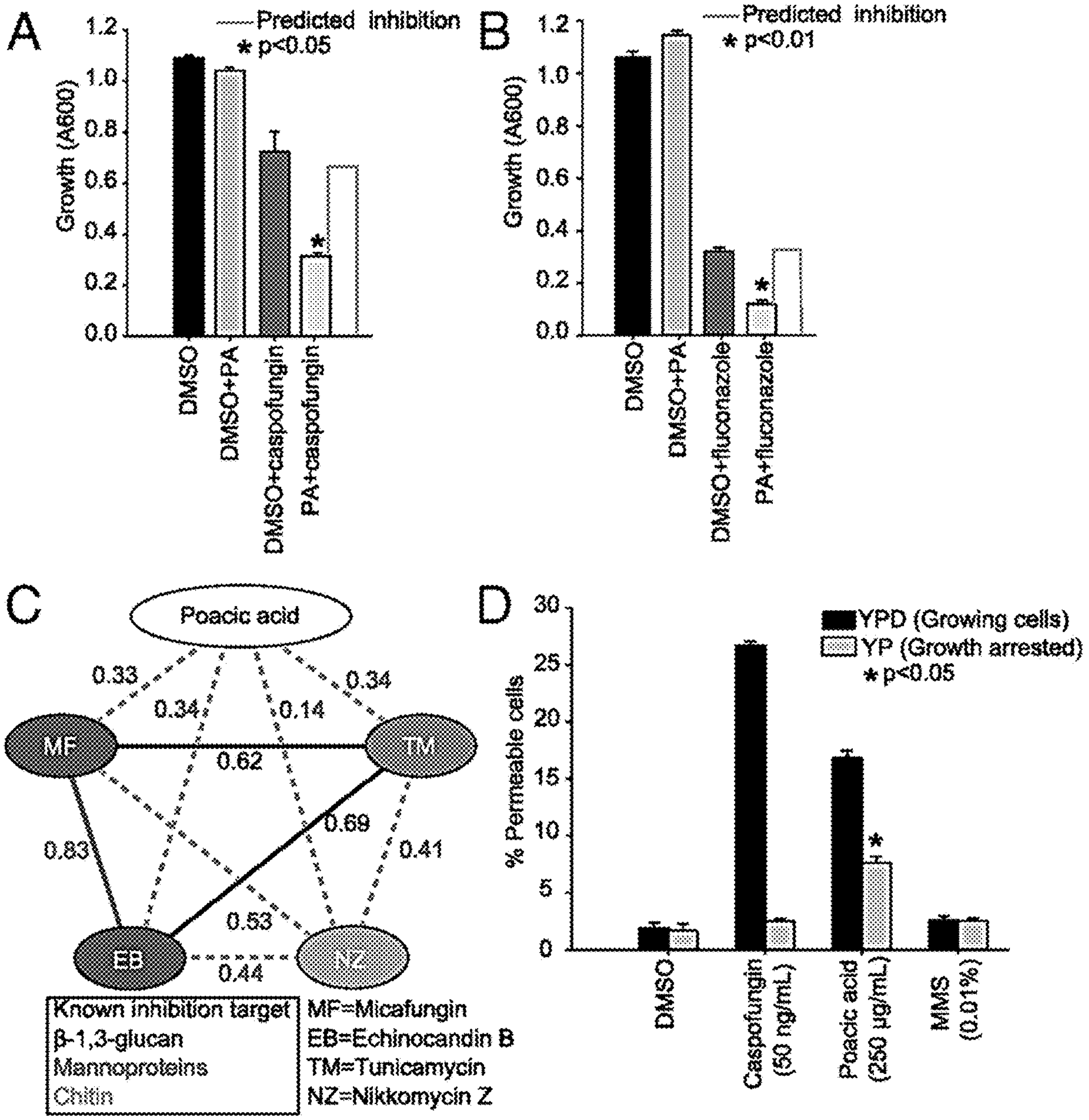
FIG. 5. Synergisms and the mode of action of poacic acid. (A) Poacic acid (125 μg/mL) is significantly synergistic with caspofungin (12.5 ng/ml). (B) Poacic acid (125 μg/mL) is also synergistic with fluconazole (3.8 μg/mL). (C) Morphological similarity between poacic acid and other cell wall-affecting agents was measured based on the correlation coefficient value (R) of their morphological profiles. (D) Poacic acid causes cell leakage within 4 h of treatment, similar to the cell wall-targeting compound caspofungin. The leakage is most apparent in actively growing cells [yeast extract peptone dextrose (YPD)] compared with cells arrested without a carbon source [yeast extract peptone (YP)]. DMSO and MMS were included as control agents that do not directly affect cell wall integrity. In arrested cells, poacic acid had significantly greater cell leakage than other treatments. One-way ANOVA and Tukey's test were used to calculate the differences between treatments (mean±SE). PA, poacic acid.
Figure 6:
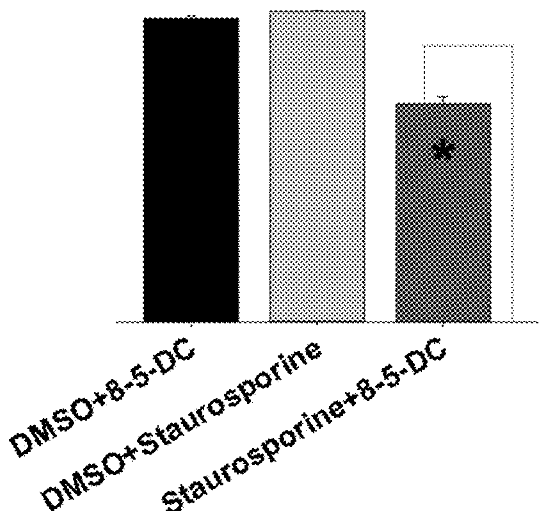
FIG. 6. Synergistic effects of poacic acid and staurosporine. Shown is a graph of growth of *Saccharomyces cerevisiae* in the presence of poacic acid (125 μg/ml) and staurosporine (100 ng/ml), alone and in combination. *=statistically significant synergism (P<0.05).

Poacic Acid is Synergistic with Drugs that Target the Cell Wall and Membrane Integrity Given that poacic acid may directly target the cell wall or the integrity signaling pathway, we tested whether the mode of action of poacic acid differed from that of the echinocandin caspofungin. Echinocandins damage the yeast cell wall by noncompetitive binding of the β-1,3-glucan synthase complex at the Fks1p subunit (Balashov et al. 2006, Johnson et al. 2012). Synergistic interactions occur with drugs targeting the same or a functionally related pathway but through different targets (Cokoi et al. 2011). We found significant synergistic effects (FIG. 5, panel A) between poacic acid and caspofungin ($P<0.05$). This interaction suggests that poacic acid targets the cell wall but does so through a mechanism distinct from that of caspofungin. Because echinocandins are also synergistic with antifungal azoles that target ergosterol biosynthesis and compromise membrane integrity (Kiraz et al. 2010), we tested and determined that poacic acid also displayed significant synergy with fluconazole (FIG. 5, panel B) ($P<0.01$). We further detected a synergy between poacic acid (125 μg/ml) and staurosporine (100 ng/ml) (FIG. 6). Staurosporine inhibits PCK1 and cell wall integrity signaling. Poacic acid was not synergistic with methyl methanesulfonate (MMS), a DNA damaging agent whose mode of action is unrelated to the cell wall.

Poacic Acid-Induced Morphologies are Unique Compared with Those from Other Cell Wall-Targeting Agent Compounds that induce similar morphological responses can be indicative of similar modes of action. To determine how similar the morphology induced by poacic acid is to that induced by other cell wall-affecting drugs, we compared their morphological profiles. Two echinocandins (micafungin and echinocandin B), both of which bind Fks1p, had morphological profiles that were highly correlated with each other, whereas poacic acid-treated cells had lower morphological correlations with these and other cell wall-affecting compounds (FIG. 5, panel C). Thus, although there is some morphological similarity with other cell wall agents, the morphological response to poacic acid suggests that it may have a mode of action that is different from that of other cell wall-targeting agents.

Poacic Acid Causes Rapid Cell Leakage

Cell wall-targeting agents, such as echinocandins, can lead to compromised cell integrity and ultimately, cell lysis from turgor pressure (Cassone et al. 1981). We investigated whether poacic acid caused cell lysis in a similar way. We tested the extent of cell permeability after 4 h of treatment with poacic acid, caspofungin, MMS, or DMSO using a propidium iodide dye that is taken up only by cells with compromised cell integrity. MMS, an agent that does not cause rapid cell wall damage, was included as a negative control. We found that both caspofungin and poacic acid caused rapid cell leakage, whereas MMS and DMSO did not (FIG. 5, panel D). When growth was arrested by depriving cells of a carbon source, the effect of caspofungin was diminished, supporting the known mode of action of echinocandins, which inhibit glucan synthesis. The effects of poacic acid were reduced in non-actively growing cells, but leakage was still significantly greater ($P<0.05$) than in all other treatments (FIG. 5, panel D). The mechanism by which poacic acid causes leakage is lessened without active growth, showing that the compound can still cause leakage in non-actively growing cells, unlike with echinocandins. This result could indicate a general disruption of cell wall integrity rather than an enzymatic target and, thus, a different mode of action.

Poacic Acid Localizes to the Cell Surface and Targets β-1,3-Glucan

Figure 7:
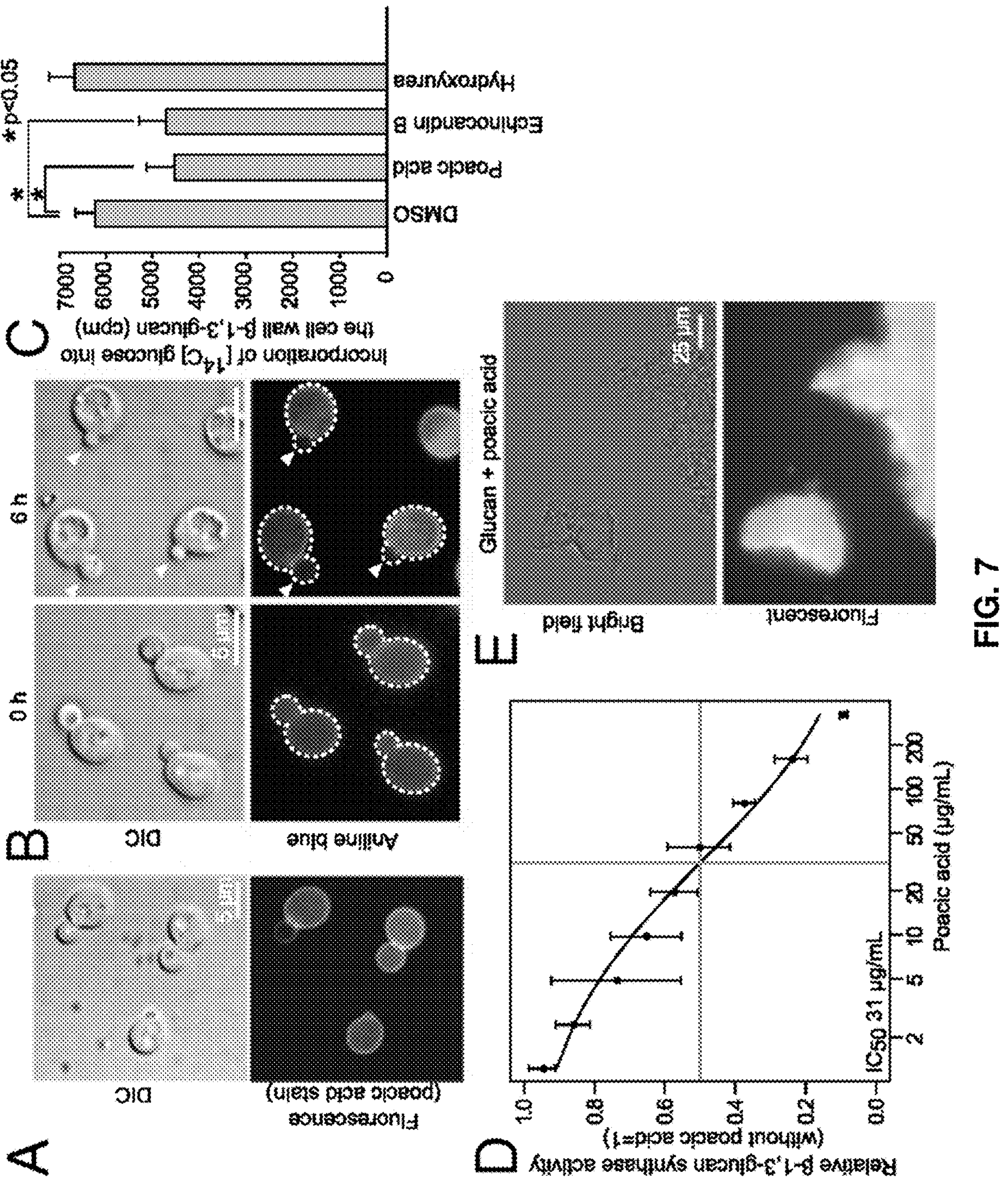
FIG. 7. Poacic acid targets β-1,3-glucan. (A) Poacic acid is fluorescent and accumulates on the cell wall. Poacic acid inhibits β-1,3-glucan in vivo as shown by (B) the decrease in signal from aniline blue staining (arrowheads) and (C) the incorporation of $^{14}$C-labeled glucose into the β-1,3-glucan layer of the cell wall (P<0.05). Concentrations of poacic acid, echinocandin B, and hydroxyurea were 250 μg/mL, 4 μg/mL, and 30 mM, respectively. (D) Poacic acid inhibits β-1,3-glucan synthase activity in vitro with an IC50 of 31 μg/mL. (E) Poacic acid directly binds purified yeast glucan. Student's t test was used to determine significant differences (mean+SD). DIC, differential interference contrast.

We next sought to determine to which cell wall component poacic acid binds by localizing the compound in treated cells. As a ferulate derivative, poacic acid is fluorescent, enabling us to visualize its accumulation at the cell surface (FIG. 7, panel A). Based on this result together with poacic acid's chemical genomic profile, morphological profile, phenotypic similarity to fks1Δ, and ability to cause cell leakage, we hypothesized that poacic acid targets the β-1,3-glucan layer and thus, rapidly compromises cell integrity, leading to cell lysis when turgor pressure bursts the weakened cell wall. The absence of chitin-related genes in both the chemical genomic and morphological profiles and the low correlation between the morphological profile of poacic acid and the chitin targeting compound nikkomycin Z led us to believe that the chitin layer is not the cell wall target of poacic acid. Furthermore, the uniform staining pattern with poacic acid is different from the calcofluor white staining of chitin, which preferentially binds the bud neck and bud scar.

Figure 8:
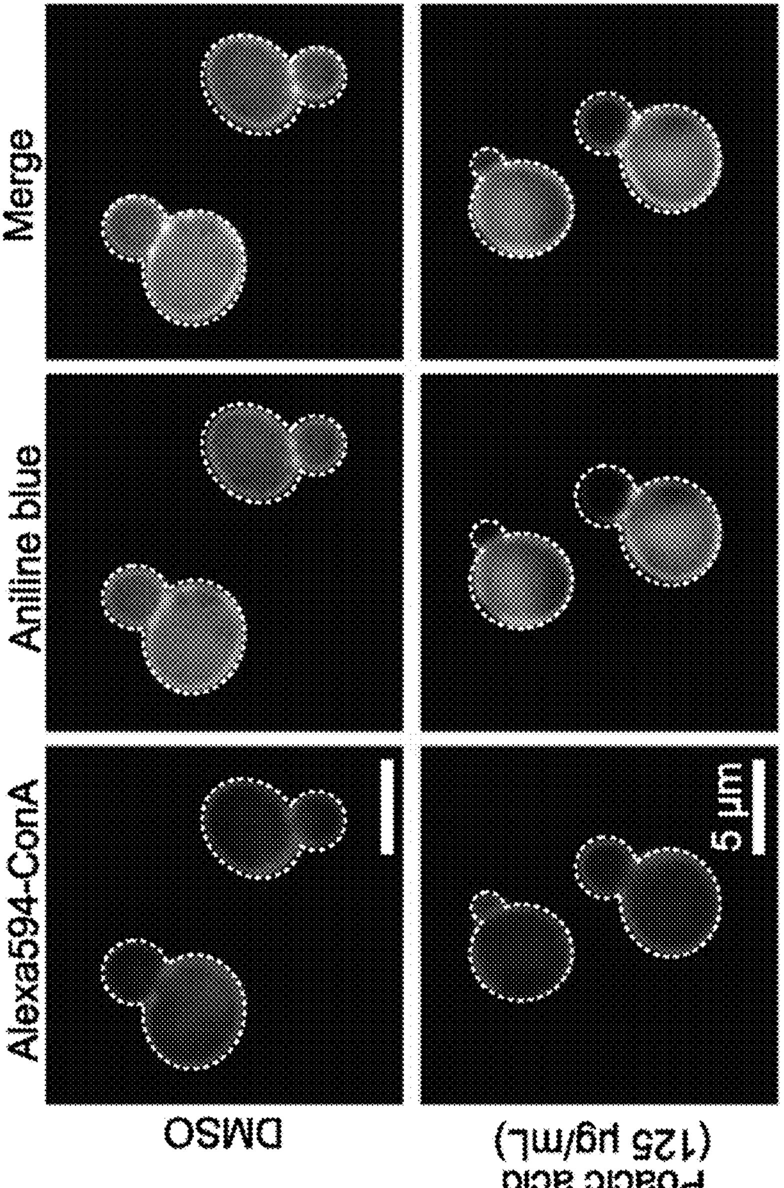
FIG. 8. Poacic acid treatment reduces glucan staining with aniline blue but has no effect on mannoprotein straining. The control strain yeast cells (his34) were grown in YPD at 25° C. until early log phase, transferred to fresh YPD medium containing poacic acid (125 μg/mL) or DMSO [0.125% (vol/vol)] as a solvent control, and cultured for 6 h. The cells were collected, and the cell wall components mannoproteins were stained with Alexa594-conjugated Con A followed by β-1,3-glucan staining with aniline blue. The cells were observed under a fluorescent microscope, and over 150 budding cells were counted according to the staining signal from three independent experiments. A Student's t test was used to determine significant differences (mean±SE; n=3).

We suggest that the mode of poacic acid action is distinct from that of the echinocandins, acting through direct binding to the glucan fibrils rather than inhibition of glucan synthase. This hypothesis is supported by observations that poacic acid does not localize specifically to the site of bud growth, like Fks1p (Utsugi et al. 2002), but rather, binds across the entire cell surface (FIG. 7, panel A). Poacic acid can inhibit β-1,3-glucan synthesis in vivo as shown by significantly decreased glucan staining in buds (FIG. 7, panel B, and FIG. 8) and significantly less 14C-glucose incorporation into the β-1,3-glucan layer after poacic acid treatment (FIG. 7, panel C). We also observed an in vitro inhibition of β-1,3-glucan synthesis after poacic acid treatment (FIG. 7, panel D). By incubating purified yeast glucan with poacic acid and observing fluorescence, we found that poacic acid directly binds β-1,3-glucan (FIG. 7, panel E). Furthermore, although poacic acid can reduce aniline blue staining of β-1,3-glucan in buds, it does not change mannoprotein staining with fluorescent dye-conjugated Con A (FIG. 8), which suggests that poacic acid acts primarily on the formation of the glucan fibrils rather than by inhibiting mannoprotein assembly in the cell wall.

Poacic Acid is an Inhibitor of Fungal and Oomycete Plant Pathogens

Figure 9:
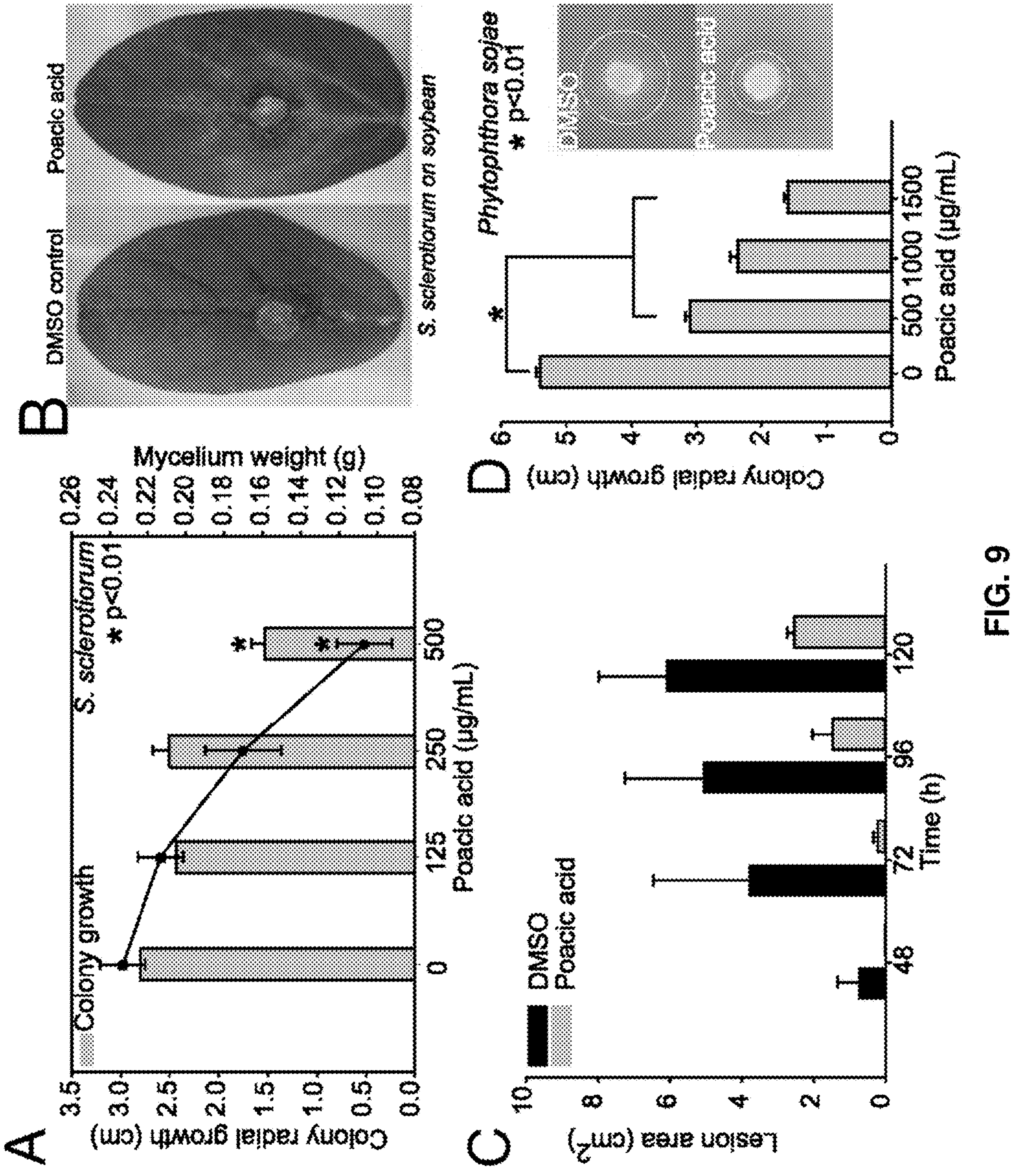
FIG. 9. Poacic acid inhibits the growth of fungal and oomycete plant pathogens. (A) Colony growth on plates and mycelia weight of *S. sclerotiorum* (strain 1980) in liquid culture were significantly inhibited by poacic acid in a dose-dependent manner. (B and C) A single aerosol treatment of poacic acid (500 μg/mL) before inoculation inhibited white mold lesion development on soybean leaves in planta. (D) Representative photographs were taken 96 h postinoculation. Poacic acid significantly inhibited colony growth of *P. sojae* (field isolate 7 d of growth). Dashed circles in Inset indicate the mycelium front after 2 d of growth. One-way ANOVA and Tukey's test were used to calculate the difference between drug treatments among treatments (mean±SE).
Figure 10:
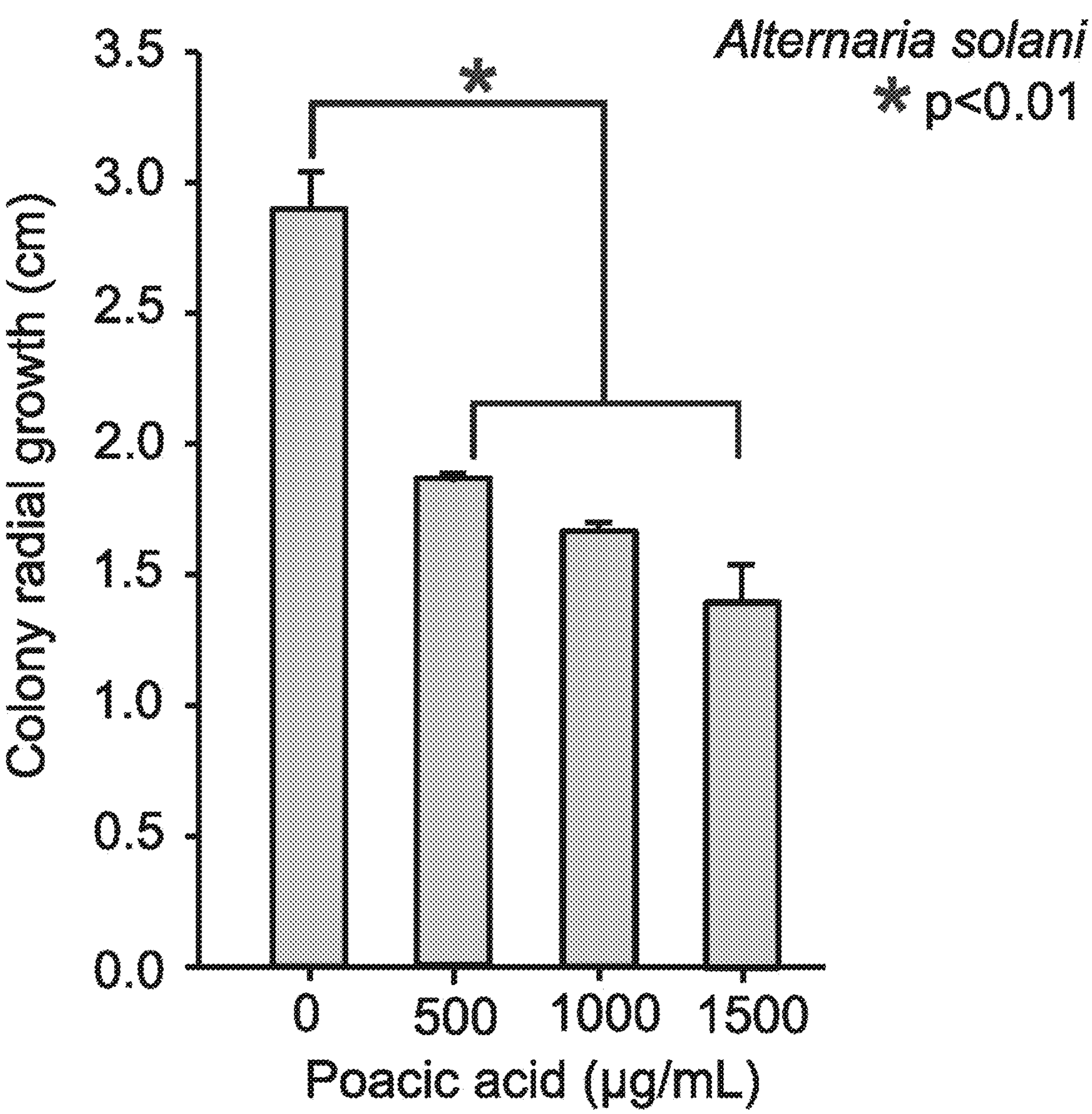
FIG. 10. Poacic acid significantly inhibits colony growth of *Alternaria solani*. Colony growth on plates of *A. solani* (field isolate) was significantly (P<0.01) inhibited by poacic acid in a dose-dependent manner. One-way ANOVA and Tukey's test were used to evaluate the difference between drug treatments among treatments (mean±SE; n=3).

As a plant-derived product, poacic acid may have a use in organic agriculture, which is presently lacking in fungicide diversity beyond copper sulfate mixtures. We initially tested the effects of poacic acid on *S. sclerotiorum*, an ascomycete fungal pathogen with an extremely broad host plant range (>400 species) and worldwide distribution. In soybeans, *S. sclerotiorum* causes *Sclerotinia* stem rot or white mold of soybean. The incorporation of poacic acid into culture media caused a significant ($P<0.01$) dose-dependent decrease in fungal growth both on agar plates and in liquid cultures, which was evidenced by decreases in colony radial growth and fungal mass (FIG. 9, panel A). We further investigated whether poacic acid could inhibit lesion development in planta on detached soybean leaves. Solvent (DMSO) control or poacic acid (500 μg/mL) solutions were applied to detached leaves before inoculation with agar plugs containing actively growing mycelia of *S. sclerotiorum*. Lesion development was monitored daily up to 120 h postinoculation. Poacic acid treatment markedly reduced lesion development over this time course compared with the control (FIG. 9, panels B and C). We also found poacic acid to be similarly effective against the ascomycete *A. solani*, which causes early blight in tomato and potato crops (FIG. 10). These data show that poacic acid inhibits fungal growth in vitro and in planta, with promising agricultural applications. Fungi generally have 30-80% glucan in their cell walls (Free 2013); similarly, oomycetes have a cell wall containing β-1,3-glucan and β-1,6-glucan, but unlike fungi, oomycete walls contain a cellulose layer rather than chitin. Oomycetes are broadly distributed, economically significant pathogens, and a fungicide that could affect both true fungi and oomycetes by disruption of the glucan layer could be of high value. We found that poacic acid significantly reduces colony growth of the oomycete *P. sojae* (FIG. 9, panel D) ($P<0.01$), a widespread pathogen that causes root and stem rot of soybeans. Given its effectiveness against both fungi and oomycetes, poacic acid may have potential as a plant-derived fungicide with broad action.

Effects of 8-5-C Diferulate

We predict that 8-5-C diferulate also has the activities and yields the effects described above for poacic acid.

Effect of Poacic Acid and 8-5-C Diferulate on Human Yeast Pathogens *Candida albicans* and *Aspergillus* Spp.

Antifungal effects of the diferulates poacic acid and 8-5-C diferulate on the human yeast pathogens *Candida albicans* and *Aspergillus* spp. will be tested in the manner described above for *Saccharomyces cerevisiae* and *Sclerotina sclerotium*. It is predicted that poacic acid and 8-5-C diferulate will have similar antifungal effects against *Candida albicans* and *Aspergillus* spp. It is further predicted that poacic acid and 8-5-C diferulate will have synergistic antifungal effects with cell-wall targeting agents against *Candida albicans* and *Aspergillus* spp.

Antimicrobial Effects of Poacic Acid and 8-5-C Diferulate Against Other Glucan-Containing Microbes We predict effectiveness of poacic acid and 8-5-C diferulate against other microbes (e.g., bacteria, etc.) that contain a glucan-comprising cell wall.

Discussion

Through chemoprospecting of lignocellulosic hydrolysates, we have identified a promising antifungal agent. Combining chemical genomic and morphological analyses, we determined that poacic acid targets β-1,3-glucan within fungal cell walls. Inhibition of glucan synthesis in vivo and in vitro and cell-wide localization and direct binding of purified glucan indicate that the compound can bind to β-1,3-glucans in the growing glucan fibrils as well as the mature wall. The cell wall dye Congo red may also bind growing glucan fibrils (Kopecka et al. 1992), but it also binds to chitin, and biochemical evidence indicates that the primary target of Congo red is chitin (Imai et al. 2005). Poacic acid targets the β-1,3-glucan layer of fungal cell walls in a manner distinct from that of other cell wall-affecting agents (e.g., caspofungin and nikkomycin Z) and, therefore, represents a previously undescribed compound targeting β-1,3-glucan. Although we found no effects of poacic acid on mannoprotein assembly, direct binding of glucan fibrils outside the plasma membrane may also result in inhibition of cell wall assemblages, such as the glucan-transglycolase Gas1p and the chitin transglycosylases Crh1p and Utr2p, that connect chitin chains to glucans, which require glucan as a substrate or cosubstrate.

Against yeast, the bioactivity of poacic acid is similar to the widely used fungicide picoxystrobin (IC50 of 308 μM), lower than thiabendazole (IC50 of 607 μM), and considerably more toxic than copper sulfate (IC50 of 2.4 mM) (Fai et al. 2009). Poacic acid may also have potential to be used combined with agricultural azoles through its documented synergism to slow the development of azole resistance. Although there are conventional fungicides effective at lower doses (e.g., captan at IC50 of 19 μM and prochloraz at IC50 of 132 μM) (Fai et al. 2009), most conventional agents are specific to either the Eumycota or Oomycota, whereas poacic acid affects both. Options for organic agriculture are limited to copper-based fungicides, which are facing increasing restrictions because of copper accumulation in soil ecosystems (Wightwick et al. 2013, Mackie et al. 2013). Furthermore, as a plant-derived phenolic acid, poacic acid would likely be rapidly broken down in the soil and would not accumulate (Chen et al. 2011).

Although it was identified from lignocellulosic hydrolysates for bioethanol fermentation, poacic acid alone is not likely to be a primary inhibitor affecting fermentation given its relatively low concentration (0.1 μM) (Table 4).

TABLE 4

Diferulates and ferulate concentration in ammonia fiber expansion-treated lignocellulosic hydrolysates (micromolar).

| Pretreatment method | 8-8-O | 8-5-O | 8-8-THF | 5-5 | 8-O-4 | 8-5-C | Poacic acid | Ferulic acid |
|---|---|---|---|---|---|---|---|---|
| 6% AFEX-treated corn stover | 3.23 | <0.2 | 0.55 | 0.16 | 0.06 | 8.58 | 0.10 | 76.6 |

AFEX, ammonia fiber expansion.

The complementary profiling methodologies that we applied to the analysis of poacic acid's effects, including chemical genomic profiling and morphological profiling, are powerful and can provide high-resolution predictions of targeted processes; this work highlights the power of the combined approach. Given the increasing throughput of both techniques thanks to advances in next generation sequencing and automated microscopy, the use of both genetic and morphological approaches in large-scale screening of drug libraries may allow unbiased whole-cell target identification with less reliance on target-centric high-throughput screening methods.

This study was designed to identify novel bioactive compounds from lignocellulosic hydrolysates. Given the goal of cellulosic ethanol production [60 billion L/y by 2022, requiring 0.6-1.2 trillion L hydrolysate/y assuming 5-10% (vol/vol) ethanol before distillation] (Westbrook et al. 2014, Lau et al. 2009), even low-abundance compounds within hydrolysates could be available in significant quantities. We have detected monomeric ferulate in hydrolysates at markedly higher levels (up to 1.7 mM in alkaline $H_2O_2$-treated corn stover). If synthesized from the recovered ferulate component posthydrolysis, poacic acid may confer greater value to lignocellulosic conversion.

LITERATURE CITED IN EXAMPLES

Abe M, Qadota H, Hirata A, Ohya Y (2003) Lack of GTP-bound Rho1p in secretory vesicles of *Saccharomyces cerevisiae*. *J Cell Biol* 162(1):85-97.

Abe M, et al. (2001) Yeast 1,3-β-glucan synthase activity is inhibited by phytosphingosine localized to the endoplasmic reticulum. *J Biol Chem* 276(29):26923-26930.

Alexander B D, Perfect J R (1997) Antifungal resistance trends towards the year 2000. Implications for therapy and new approaches. *Drugs* 54(5):657-678.

Andrusiak K (2012) Adapting *S. cerevisiae* chemical genomics for identifying the modes of action of natural compounds. Masters thesis (University of Toronto, Toronto).

Altizer S, Ostfeld R S, Johnson P T J, Kutz S, Harvell C D (2013) Climate change and infectious diseases: From evidence to a predictive framework. *Science* 341(6145): 514-519.

Avenot H F, Sellam A, Karaoglanidis G, Michailides T J (2008) Characterization of mutations in the iron-sulphur subunit of succinate dehydrogenase correlating with Boscalid resistance in *Alternaria alternata* from California pistachio. *Phytopathology* 98(6):736-742.

Balashov, S. V., Park, S. & Perlin, D. S. Assessing Resistance to the Echinocandin Antifungal Drug Caspofungin in *Candida albicans* by Profiling Mutations in FKS1. *Antimicrob. Agents Chemother.* 50, 2058-2063 (2006).

Baranowski, J. D., Davidson, P. M., Nagel, C. W. & Branen, A. L. Inhibition of *Saccharomyces cerevisiae* by naturallyl occurring hydroxycinnamates. *J. Food Sci.* 45, 592-594 (1980).

Boyle E I, et al. (2004) GO:TermFinder-open source software for accessing Gene Ontology information and finding significantly enriched Gene Ontology terms associated with a list of genes. *Bioinformatics* 20(18):3710-3715.

Bunzel, M., Ralph, J., Marita, J. M., Hatfield, R. D. & Steinhart, H. Diferulates as structural components in soluble and insoluble cereal dietary fibre. *J. Sci. Food Agric.* 81, 653-660 (2001).

Cassone A, Mason R E, Kerridge D (1981) Lysis of growing yeast-form cells of *Candida albicans* by echinocandin: A cytological study. *Sabouraudia* 19(2):97-110.

Chen L, et al. (2011) *Trichoderma harzianum* SQR-T037 rapidly degrades allelochemicals in rhizospheres of continuously cropped cucumbers. *Appl Microbiol Biotechnol* 89(5):1653-1663.

Cokol M, et al. (2011) Systematic exploration of synergistic drug pairs. *Mol Syst Biol* 7(2011):544.

Costanzo, M. et al. The Genetic Landscape of a Cell. *Science* 327, 425-431 (2010).

DePristo, M. A. et al. A framework for variation discovery and genotyping using next-generation DNA sequencing data. *Nat. Genet.* 43, 491-498 (2011).

Fai P B, Grant A (2009) A rapid resazurin bioassay for assessing the toxicity of fungicides. *Chemosphere* 74(9): 1165-1170.

FitzPatrick, M., Champagne, P., Cunningham, M. F. & Whitney, R. A. A biorefinery processing perspective: Treatment of lignocellulosic materials for the production of value-added products. *Bioresour. Technol.* 101, 8915-8922 (2010).

Free S J (2013) Fungal cell wall organization and biosynthesis. Adv Genet 81:33-82.

Fung S Y, Sofiyev V, Schneiderman J, Hirschfeld A F, Victor R E, Woods K, Piotrowski J S, Deshpande R, Li S C, de Voogd N J, Myers C L, Boone C, Andersen R J, Turvey S E. Unbiased screening of marine sponge extracts for anti-inflammatory agents combined with chemical genomics identifies girolline as an inhibitor of protein synthesis. *ACS Chem Biol.* 2014 Jan. 17; 9(1):247-57.

Funk, C., Braune, A., Grabber, J. H., Steinhart, H. & Bunzel, M. Moderate Ferulate and Diferulate Levels Do Not Impede Maize Cell Wall Degradation by Human Intestinal Microbiota. *J. Agric. Food Chem.* 55, 2418-2423 (2007).

Garrett K A, Dendy S P, Frank E E, Rouse M N, Travers S E (2006) Climate change effects on plant disease: Genomes to ecosystems. *Annu Rev Phytopathol* 44(1): 489-509.

Gnansounou, E. & Dauriat, A. Techno-economic analysis of lignocellulosic ethanol: A review. *Bioresour. Technol.* 101, 4980-4991 (2010).

Hatfield, R. D., Ralph, J. & Grabber, J. H. Cell wall cross-linking by ferulates and diferulates in grasses. *J. Sci. Food Agric.* 79, 403-407 (1999).

Heer D, Sauer U (2008) Identification of furfural as a key toxin in lignocellulosic hydrolysates and evolution of a tolerant yeast strain. *Microb Biotechnol* 1(6):497-506.

Ho, C. H. et al. Combining functional genomics and chemical biology to identify targets of bioactive compounds. *Curr. Opin. Chem. Biol.* 15, 66-78 (2011).

Imai K, Noda Y, Adachi H, Yoda K (2005) A novel endoplasmic reticulum membrane protein Rcr1 regulates chitin deposition in the cell wall of *Saccharomyces cerevisiae. J Biol Chem* 280(9):8275-8284.

Inoue S B, et al. (1995) Characterization and gene cloning of 1,3-β-D-glucan synthase from *Saccharomyces cerevisiae. Eur J Biochem* 231(3): 845-854.

Iwaki, A., Ohnuki, S., Suga, Y., Izawa, S. & Ohya, Y. Vanillin inhibits translation and induces messenger ribonucleoprotein (mRNP) granule formation in *Saccharomyces cerevisiae*: application and validation of high-content, image-based profiling. *PloS One* 8, e61748 (2013).

Jayakody L N, Hayashi N, Kitagaki H (2011) Identification of glycolaldehyde as the key inhibitor of bioethanol fermentation by yeast and genome-wide analysis of its toxicity. *Biotechnol Lett* 33(2):285-292.

Jesch, S. A., Gaspar, M. L., Stefan, C. J., Aregullin, M. A. & Henry, S. A. Interruption of Inositol Sphingolipid Synthesis Triggers Stt4p-dependent Protein Kinase C Signaling. *J. Biol. Chem.* 285, 41947-41960 (2010).

Jo W J, et al. (2008) Identification of genes involved in the toxic response of *Saccharomyces cerevisiae* against iron and copper overload by parallel analysis of deletion mutants. *Toxicol Sci* 101(1):140-151.

Johnson, M. E. & Edlind, T. D. Topological and Mutational Analysis of *Saccharomyces cerevisiae* Fks1. *Eukaryot. Cell* 11, 952-960 (2012).

Kiraz N, et al. (2010) Synergistic activities of three triazoles with caspofungin against *Candida glabrata* isolates determined by time-kill, Etest, and disk diffusion methods. *Antimicrob Agents Chemother* 54(5):2244-2247.

Kitagaki H, Wu H, Shimoi H, Ito K (2002) Two homologous genes, DCW1 (YKL046c) and DFG5, are essential for cell growth and encode glycosylphosphatidylinositol (GPI)-anchored membrane proteins required for cell wall biogenesis in *Saccharomyces cerevisiae. Mol Microbiol* 46(4): 1011-1022.

Kopecká M, Gabriel M (1992) The influence of congo red on the cell wall and (1-3)-beta-D-glucan microfibril biogenesis in *Saccharomyces cerevisiae. Arch Microbiol* 158(2): 115-126.

Koppram, R., Tomás-Pejó, E., Xiros, C. & Olsson, L. Lignocellulosic ethanol production at high-gravity: challenges and perspectives. *Trends Biotechnol.* 32, 46-53 (2014).

Lau M W, Dale B E (2009) Cellulosic ethanol production from AFEX-treated corn stover using *Saccharomyces cerevisiae* 424A(LNH-ST). *Proc Natl Acad Sci USA* 106(5):1368-1373.

Leroch M, Kretschmer M, Hahn M (2011) Fungicide resistance phenotypes of *Botrytis cinerea* isolates from commercial vineyards in south west Germany. *J Phytopathol* 159(1):63-65.

Li, H. & Durbin, R. Fast and accurate short read alignment with Burrows-Wheeler transform. *Bioinforma*. Oxf. Engl. 25, 1754-1760 (2009).

Lu F, Wei L, Azarpira A, Ralph J. Rapid syntheses of dehydrodiferulates via biomimetic radical coupling reactions of ethyl ferulate. *J Agric Food Chem.* 2012 Aug. 29; 60(34):8272-7.

Markovich, S., Yekutiel, A., Shalit, I., Shadkchan, Y. & Osherov, N. Genomic Approach to Identification of Mutations Affecting Caspofungin Susceptibility in *Saccharomyces cerevisiae. Antimicrob. Agents Chemother.* 48, 3871-3876 (2004).

Mackie K A, Müller T, Zikeli S, Kandeler E (2013) Long-term copper application in an organic vineyard modifies spatial distribution of soil micro-organisms. *Soil Biol Biochem* 65(2013):245-253.

Ohkuni, K., Okuda, A. & Kikuchi, A. Yeast Nap1-binding protein Nbp2p is required for mitotic growth at high temperatures and for cell wall integrity. Genetics 165, 517-529 (2003).

Ohnuki, S., Oka, S., Nogami, S. & Ohya, Y. High-Content, Image-Based Screening for Drug Targets in Yeast. *PLOS ONE* 5, e10177 (2010).

Ohnuki, S. et al. Analysis of the biological activity of a novel 24-membered macrolide JBIR-19 in *Saccharomyces cerevisiae* by the morphological imaging program CalMorph. *FEMS Yeast Res.* 12, 293-304 (2012).

Ohya, Y. et al. High-dimensional and large-scale phenotyping of yeast mutants. *Proc. Natl. Acad. Sci. U.S.A* 102, 19015-19020 (2005).

Okada, H., Ohnuki, S., Roncero, C., Konopka, J. B. & Ohya, Y. Distinct roles of cell wall biogenesis in yeast morphogenesis as revealed by multivariate analysis of high-dimensional morphometric data. *Mol. Biol. Cell* 25, 222-233 (2014)

Okada H, Ohya Y (2015) Cold Spring Harbor Protocols (Cold Spring Harbor Lab Press, Plainview, NY).

Palmqvist, E. & Hahn-Hägerdal, B. Fermentation of lignocellulosic hydrolysates. II: inhibitors and mechanisms of inhibition. Bioresour. *Technol.* 74, 25-33 (2000).

Parsons, A. et al. Exploring the Mode-of-Action of Bioactive Compounds by Chemical-Genetic Profiling in Yeast. *Cell* 126, 611-625 (2006).

Peltier, A. J. et al. Biology, Yield loss and Control of *Sclerotinia* Stem Rot of Soybean. *J. Integr. Pest Manag.* 3, B1-B7 (2012).

Piotrowski, J. S. et al. Death by a thousand cuts: the challenges and diverse landscape of lignocellulosic hydrolysate inhibitors. *Front. Microbiol.* 5, (2014).

Piotrowski, J. S., Morford, S. L. & Rillig, M. C. Inhibition of colonization by a native arbuscular mycorrhizal fungal community via *Populus trichocarpa* litter, litter extract, and soluble phenolic compounds. *Soil Biol. Biochem.* 40, 709-717 (2008).

Piotrowski J S, Okada H, Lu F, Li S C, Hinchman L, Ranjan A, Smith D L, Higbee A J, Ulbrich A, Coon J J, Deshpande R, Bukhman Y V, Mcllwain S, Ong I M, Myers C L, Boone C, Landick R, Ralph J, Kabbage M, Ohya Y. Plant-derived antifungal agent poacic acid targets β-1,3-glucan. *Proc Natl Acad Sci USA.* 2015 Mar. 24; 112(12): E1490-7.

Ralph J, Quideau S, Grabber J H, Hatfield R D (1994) Identification and synthesis of new ferulic acid dehydrodimers present in grass cell walls. *J Chem Soc* 23:3485-3498.

Ralph J, et al. (1998) Cell wall cross-linking in grasses by ferulates and diferulates.

Reinoso-Martín, C., Schüller, C., Schuetzer-Muehlbauer, M. & Kuchler, K. The yeast protein kinase C cell integrity pathway mediates tolerance to the antifungal drug caspofungin through activation of Slt2p mitogen-activated protein kinase signaling. *Eukaryot. Cell* 2, 1200-1210 (2003).

Robinson D G, Chen W, Storey J D, Gresham D (2014) Design and analysis of Bar-seq experiments. G3 (Bethesda) 4(1):11-18.

Robinson M D, McCarthy D J, Smyth G K (2010) edgeR: A Bioconductor package for differential expression analysis of digital gene expression data. *Bioinformatics* 26(1): 139-140.

Rogers B, et al. (2001) The pleitropic drug ABC transporters from *Saccharomyces cerevisiae. J Mol Microbiol Biotechnol* 3(2):207-214.

Santiago, R. et al. Diferulate Content of Maize Sheaths Is Associated with Resistance to the Mediterranean Corn Borer Sesamia nonagrioides (Lepidoptera: Noctuidae). *J. Agric. Food Chem.* 54, 9140-9144 (2006).

Sarma, B. K. & Singh, U. P. Ferulic acid may prevent infection of *Cicer arietinum* by *Sclerotium rolfsii. World J. Microbiol. Biotechnol.* 19, 123-127 (2003).

Sato T K, et al. (2014) Harnessing genetic diversity in *Saccharomyces cerevisiae* for improved fermentation of xylose in hydrolysates of alkaline hydrogen peroxide pretreated biomass. *Appl Environ Microbiol* 80(2):540-554.

Skerker J M, et al. (2013) Dissecting a complex chemical stress: Chemogenomic profiling of plant hydrolysates. *Mol Syst Biol* 9:674.

Smith A M, et al. (2009) Quantitative phenotyping via deep barcode sequencing. *Genome Res* 19(10):1836-1842.

Sun, Y. & Cheng, J. Hydrolysis of lignocellulosic materials for ethanol production: a review. *Bioresour. Technol.* 83, 1-11 (2002).

Surma M A, et al. (2013) A lipid E-MAP identifies Ubx2 as a critical regulator of lipid saturation and lipid bilayer stress. *Mol Cell* 51(4):519-530.

Utsugi, T. et al. Movement of yeast 1,3-β-glucan synthase is essential for uniform cell wall synthesis. *Genes Cells* 7, 1-9 (2002).

Vismeh, R. et al. Profiling of diferulates (plant cell wall cross-linkers) using ultrahigh-performance liquid chromatography-tandem mass spectrometry. *Analyst* 138, 6683-6692 (2013).

Watanabe D, Abe M, Ohya Y (2001) Yeast Lrg1p acts as a specialized RhoGAP regulating 1,3-β-glucan synthesis. *Yeast* 18(10):943-951.

Westbrook J, Barter G E, Manley D K, West T H (2014) A parametric analysis of future ethanol use in the light-duty transportation sector: Can the US meet its Renewable Fuel Standard goals without an enforcement mechanism? *Energy Policy* 65(2014):419-431.

Wightwick A M, Salzman S A, Reichman S M, Allinson G, Menzies N W (2013) Effects of copper fungicide residues on the microbial function of vineyard soils. *Environ Sci Pollut Res Int* 20(3): 1574-1585.

Yvert G, et al. (2013) Single-cell phenomics reveals intra-species variation of phenotypic noise in yeast. *BMC Syst Biol* 7(1):54.

What is claimed is:

1. A method of inhibiting growth of a microorganism in planta, the method comprising applying to a plant an amount of a compound effective to inhibit growth of the microorganism in the plant, wherein the microorganism is at least one of a fungus and an oomycete comprising a β-1,3-glucan-containing cell wall, wherein the compound is:

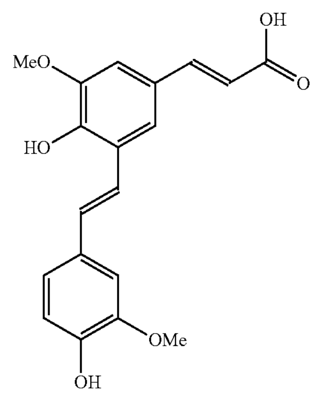 [SMILES: COc1cc(/C=C/c2cc(/C=C/C(=O)O)cc(OC)c2O)ccc1O]

or a salt thereof.

2. The method of claim 1, wherein the applying comprises externally applying the compound to a surface of the plant.

3. The method of claim 1, wherein the applying comprises externally applying the compound to a leaf of the plant.

4. The method of claim 1, wherein the microorganism comprises at least one of *Sclerotinia sclerotiorum, Phytophthora sojae*, and *Alternaria solani.*

5. The method of claim 1, wherein the applying comprises externally applying the compound to a surface of the plant, wherein the microorganism comprises at least one of *Sclerotinia sclerotiorum, Phytophthora sojae*, and *Alternaria solani.*

6. The method of claim 1, wherein the applying comprises externally applying the compound to a leaf of the plant, wherein the microorganism comprises at least one of *Sclerotinia sclerotiorum, Phytophthora sojae*, and *Alternaria solani.*

7. A method of inhibiting growth of a microorganism, the method comprising contacting the microorganism with an amount of a compound effective to inhibit growth of the microorganism, wherein the microorganism is at least one of a fungus and an oomycete comprising a β-1,3-glucan-containing cell wall, wherein the compound is:
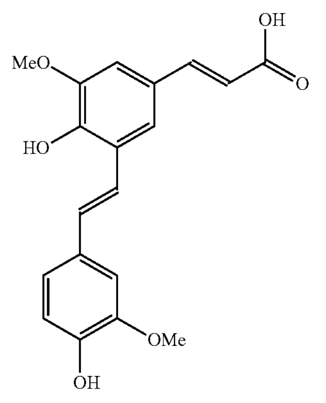 [SMILES: COc1cc(/C=C/c2cc(/C=C/C(=O)O)cc(OC)c2O)ccc1O]
or a salt thereof.
* * * * *